US012595237B2

(12) United States Patent
Li et al.

(10) Patent No.: US 12,595,237 B2
(45) Date of Patent: *Apr. 7, 2026

(54) LAMOTRIGINE HYDRATE CRYSTAL FORM, PREPARATION METHOD THEREFOR, AND COMPOSITION CONTAINING SAME

(71) Applicant: Shanghai Aucta Pharmaceuticals Co., Ltd., Shanghai (CN)

(72) Inventors: Shoufeng Li, Piscataway, NJ (US); Yong Wang, Shanghai (CN); Boli Li, Shanghai (CN)

(73) Assignee: SHANGHAI AUCTA PHARMACEUTICALS CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/555,659

(22) PCT Filed: Apr. 18, 2022

(86) PCT No.: PCT/CN2022/087326
§ 371 (c)(1),
(2) Date: Oct. 16, 2023

(87) PCT Pub. No.: WO2022/218437
PCT Pub. Date: Oct. 20, 2022

(65) Prior Publication Data
US 2024/0207280 A1 Jun. 27, 2024

Related U.S. Application Data

(63) Continuation of application No. 17/366,295, filed on Jul. 2, 2021, now Pat. No. 11,447,456.

(30) Foreign Application Priority Data

Apr. 16, 2021 (CN) .......................... 202110412683.1

(51) Int. Cl.
| | |
|---|---|
| C07D 253/075 | (2006.01) |
| A61K 9/08 | (2006.01) |
| A61K 9/10 | (2006.01) |
| A61K 9/20 | (2006.01) |
| A61K 9/48 | (2006.01) |
| A61K 31/165 | (2006.01) |
| A61K 31/357 | (2006.01) |
| A61K 31/53 | (2006.01) |
| A61K 31/5513 | (2006.01) |
| A61K 47/02 | (2006.01) |
| A61K 47/12 | (2006.01) |
| A61K 47/14 | (2017.01) |
| A61K 47/26 | (2006.01) |
| A61K 47/32 | (2006.01) |
| A61K 47/38 | (2006.01) |
| C07B 63/04 | (2006.01) |

(52) U.S. Cl.
CPC ............ *C07D 253/075* (2013.01); *A61K 9/08* (2013.01); *A61K 9/10* (2013.01); *A61K 9/2018* (2013.01); *A61K 9/48* (2013.01); *A61K 31/165* (2013.01); *A61K 31/357* (2013.01); *A61K 31/53* (2013.01); *A61K 31/5513* (2013.01); *A61K 47/02* (2013.01); *A61K 47/12* (2013.01); *A61K 47/14* (2013.01); *A61K 47/26* (2013.01); *A61K 47/32* (2013.01); *A61K 47/38* (2013.01); *C07B 63/04* (2013.01); *C07B 2200/13* (2013.01)

(58) Field of Classification Search
CPC ...................................................... A61K 31/53
See application file for complete search history.

(56) References Cited

U.S. PATENT DOCUMENTS

| | | | |
|---|---|---|---|
| 6,861,426 B2 | 3/2005 | Garti et al. | |
| 7,390,807 B2 | 6/2008 | Garti et al. | |
| 7,629,331 B2 | 12/2009 | Pipkin et al. | |
| 8,486,927 B2 | 7/2013 | Hanna et al. | |
| 10,653,626 B2 * | 5/2020 | Lu ........................ A61K 9/0095 |
| 11,447,456 B1 * | 9/2022 | Li, Sr. ................... A61K 47/38 |
| 2004/0192690 A1 * | 9/2004 | Buxton ................ A61K 9/2031 |
| | | | 514/242 |
| 2005/0238724 A1 | 10/2005 | Aronhime et al. | |
| 2009/0312544 A1 | 12/2009 | Van Deynse et al. | |
| 2012/0142919 A1 * | 6/2012 | Arnalot Aguilar .......................... |
| | | | C07D 253/075 |
| | | | 544/182 |
| 2020/0375995 A1 * | 12/2020 | Sudhakar ............... A61K 47/36 |

FOREIGN PATENT DOCUMENTS

| | | |
|---|---|---|
| CN | 101506178 A | 8/2009 |
| CN | 101795673 A | 8/2010 |
| CN | 104940930 A | 9/2015 |

(Continued)

OTHER PUBLICATIONS

Wang (Biomed Research International 7810196/1-7810196/9 published 2016) (Year: 2016).*

(Continued)

*Primary Examiner* — George W Kosturko
(74) *Attorney, Agent, or Firm* — FOX ROTHSCHILD LLP

(57) ABSTRACT

The present invention relates to a crystalline form of a lamotrigine hydrate, a method for preparing the same and a composition comprising the same, and in particular, to a lamotrigine hydrate form A, a method for preparing the lamotrigine hydrate form A and a composition comprising the lamotrigine hydrate form A.

13 Claims, 4 Drawing Sheets

(56)     References Cited

FOREIGN PATENT DOCUMENTS

| | | | | | |
|---|---|---|---|---|---|
| CN | 106491539 A | * | 3/2017 | ............. | A61K 31/53 |
| CN | 110545818 A | | 12/2019 | | |
| CN | 113214177 A | | 8/2021 | | |
| WO | WO-9415607 A1 | * | 7/1994 | ............. | A61P 25/16 |
| WO | WO-2005003104 A2 | * | 1/2005 | ......... | C07D 253/075 |
| WO | 2008068619 A2 | | 6/2008 | | |
| WO | 2016086193 A1 | | 6/2016 | | |
| WO | WO-2018071547 A1 | * | 4/2018 | ............. | A61K 9/10 |

OTHER PUBLICATIONS

Allen, L.V., "Lamotrigine 1 mg/ml Oral Suspension", U.S. Pharmacist, May 15, 2015, vol. 40, No. 5, ISSN: 0148-4818, pp. 64-65.
Rani, et al: "Full Factorial Design in Formulation of Lamotrigine Suspension Using Locust Bean Gum", Int. J. Sci., Dec. 31, 2013, vol. 11, No. 2, ISSN: 0972-768X, pp. 751-760.

* cited by examiner

LAMOTRIGINE HYDRATE CRYSTAL FORM, PREPARATION METHOD THEREFOR, AND COMPOSITION CONTAINING SAME

CROSS REFERENCE TO RELATED APPLICATIONS

This application is based on and claims priorities to Chinese Application No. 202110412683.1 field on Apr. 16, 2021, and U.S. application Ser. No. 17/366,295 filed on Jul. 2, 2021, the disclosures of which are both incorporated herein.

TECHNICAL FIELD

The present invention relates to a crystalline form of a lamotrigine hydrate, a method for preparing the same and a composition comprising the same, and in particular, to a lamotrigine hydrate form A, a method for preparing the lamotrigine hydrate form A and a composition comprising the lamotrigine hydrate form A.

BACKGROUND

Epilepsy is one of the most common nervous system diseases. An epileptic attack may lead to progressive loss in brain function, causing cognitive impairment and mental decline. A sudden epileptic attack tends to cause accidental injuries, while a sustained epileptic attack may endanger life and seriously affect the quality of life of a patient, which generally leads to lifelong medication.

Lamotrigine (under the trade name Lamictal) plays an anti-epileptic role mainly by blocking voltage-gated sodium channels, reducing the influx of sodium, and increasing the stability of neurons. Lamotrigine was marketed in Europe and the United States in 1991 and 1994, respectively. Currently, lamotrigine is used in monotherapy or adjunctive therapy for various types of epilepsy, especially in infant, adolescent and elderly patients, with an efficacy comparable to that of phenytoin and carbamazepine.

At present, 4 dosage forms of lamotrigine have been approved to go into the market in China and abroad: a common tablet, a chewable tablet, an orally disintegrating tablet and a slow-release tablet. As there is no marketable oral liquid formulation of lamotrigine, it is often required to crush a lamotrigine tablet into powder to prepare a liquid formulation in use, in order to facilitate oral administration to children patients or patients with dysphagia. However, this extemporaneous formulation may easily result in inaccurate dosing as well as drug contamination.

Lamotrigine is a BCS (biopharmaceutical classification system) class II drug molecule, which has a poor solubility in aqueous media, although decreasing pH may increase solubility to some extent, with only a limited effect. The Chinese Patent Applications CN201510288845.X and CN201510350210.8 disclose medical prescriptions of a lamotrigine oral liquid formulation and a method for preparing the same, where the drug concentration of the formulation is less than 2 mg/ml, which cannot meet clinical requirements. In case that a high concentration of medical prescription is required, it is necessary to add an organic solvent, which is not favorable for oral administration to children.

It is also not desirable to develop a suspension with an anhydrous lamotrigine. The applicant has found by experiments that although no bulk crystal was found on a newly prepared lamotrigine suspension that was made through a common method, after standing at room temperature for 3 days, a large number of bulk crystals appeared and tended to become larger over time, resulting in inaccurate dosing for patients. The Chinese Patent Application CN201611175342.2A discloses a method for inhibiting a hydrate, but such an inhibiting effect can only be maintained for 24 hours, causing inconvenience in long-term medication of patients.

Various properties of a pharmaceutical active ingredient, such as the melting point, solubility, stability and bioavailability, may be affected by a crystalline state thereof. Since eutectics or hydrates of a drug may effectively improve the crystallization and physicochemical properties of the drug through a hydrogen bond or other non-covalent bonds, without compromising the active ingredients of the drug, they have become focuses in the development of solid pharmaceutical formulations.

So far, a variety of lamotrigine eutectics have been reported. Lamotrigine salts that have been reported include 1:1 lamotrigine-4-hydroxybenzoic acid, 1:1 lamotrigine-saccharin, 1:3 lamotrigine-acetic acid, 1:1 lamotrigine-propionic acid, 2:1 lamotrigine-adipic acid, 2:1 lamotrigine-malic acid, 1:1 lamotrigine-methyl p-hydroxybenzoate, 1:1 lamotrigine-nicotine, 1:1:1 lamotrigine-nicotine monohydrate, and 1:1 lamotrigine-acetamide. Lamotrigine solvates that have been reported include 1:2 lamotrigine methanol solvate, and 1:1:1 lamotrigine ethanol monohydrate. However, as no liquid dosage form of the above eutectics has been developed, the problem of inaccurate dosing of lamotrigine is still yet to solve.

There are problems with current lamotrigine formulations, such as inaccurate dosing, low loading of the solution form, and poor physical stability of the suspension.

SUMMARY OF THE INVENTION

In a first aspect, the present invention provides a lamotrigine hydrate form A, wherein an XRPD pattern of the lamotrigine hydrate form A includes characteristic peaks at diffraction angles (2θ) of about 11.5±0.2, 13.4±0.2, 15.0±0.2, 16.5±0.2, 19.2±0.2, 26.9±0.2, and 27.7±0.2 degrees, and has no characteristic peak(s) at one or more of diffraction angles (2θ) of about 15.9±0.2, 20.5=0.2, 23.5±0.2, 28.2±0.2, and 30.7±0.2 degrees.

In some embodiments, the XRPD pattern of the lamotrigine hydrate form A comprises characteristic peaks at diffraction angles (2θ) substantially the same as diffraction angles shown in FIG. 1; or the XRPD pattern of the lamotrigine hydrate form A has XRPD peak positions substantially the same as XRPD peak positions shown in FIG. 1.

In some embodiments, the lamotrigine hydrate form A has a purity of at least about 80%.

In a second aspect, the present invention provides a method for preparing a suspension of a lamotrigine hydrate form A, comprising the steps of: adding lamotrigine particles and a thickener to an aqueous phase; dispersing uniformly; and standing at a low temperature to obtain a suspension comprising the lamotrigine hydrate form A, wherein the lamotrigine particles have a particle size (D90) of about 1-30 μm.

In a third aspect, the present invention provides a method for preparing a lamotrigine hydrate form A, comprising filtering the suspension of the lamotrigine hydrate form A of the present invention, to obtain the lamotrigine hydrate form A.

In some embodiments, the lamotrigine particles have a particle size (D90) of about 8-12 μm.

In some embodiments, the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations. In some embodiments, based on about 10 parts by weight of the lamotrigine particles, the thickener is about 1-7 parts by weight.

In some embodiments, the aqueous phase is purified water or comprises purified water and one or more of the following: an essence, a pH modifier and a sweetener. In some embodiments, based on about 10 parts by weight of the lamotrigine particles, the aqueous phase is about 100-5000 parts by weight.

In some embodiments, the dispersing uniformly is implemented by mechanical stirring, magnetic stirring, and/or manual shaking for about 1-120 minutes.

In some embodiments, the low temperature is lower than about 25° C. The standing at a low temperature is carried out for at least about 30 minutes.

In some embodiments, the dispersing uniformly is separated by a time interval of up to about 12 hours from the standing at a low temperature.

In some embodiments, the suspension may be applied as a suspension.

In some embodiments, more than about 80% of lamotrigine exists in a form of the lamotrigine hydrate form A.

In a fourth aspect, the present invention provides a composition comprising the lamotrigine hydrate form A of the present invention and one or more pharmaceutically acceptable excipients.

In some embodiments, the composition further comprises one or more additional medicaments selected from the group consisting of oxcarbazepine, carbamazepine, topiramate, and lacosamide.

In some embodiments, the composition is in a dosage form selected from the group consisting of a tablet, a capsule, a powder, and a suspension.

In some embodiments, more than about 80% of lamotrigine in the composition exists in a form of the lamotrigine hydrate form A.

In some embodiments, the pharmaceutically acceptable excipients are selected from the group consisting of one or more of a thickener, a filler, a sweetener, a pH modifier and a preservative.

In some embodiments, the composition of the present invention comprises:

about 10 parts by weight of the lamotrigine hydrate form A;

about 1-5 parts by weight of xanthan gum;

about 20-60 parts by weight of mannitol;

about 1-3 parts by weight of sucralose;

about 2-5 parts by weight of sodium dihydrogen phosphate; and about 1-3 parts by weight of a combination of sodium methylparaben and sodium propylparaben, wherein a weight ratio of the sodium methylparaben to the sodium propylparaben is about 9:1.

In a fifth aspect, the present invention provides a suspension comprising a lamotrigine hydrate form A, the lamotrigine hydrate form A, a solid form comprising the lamotrigine hydrate form A or a composition comprising the lamotrigine hydrate form A, prepared by the method of the present invention.

In some embodiments, in the suspension comprising the lamotrigine hydrate form A, the lamotrigine hydrate form A, the solid form comprising the lamotrigine hydrate form A or the composition comprising the lamotrigine hydrate form A, more than about 80% of lamotrigine exists in a form of the lamotrigine hydrate form A.

In a sixth aspect, the present invention provides a method for treating a nervous system disease, comprising administering a therapeutically effective amount of the lamotrigine hydrate form A of the present invention or the composition of the present invention to a subject in need thereof.

In a seventh aspect, the present invention provides a use of the lamotrigine hydrate form A of the present invention or the composition of the present invention in preparation of a medicament for treating a nervous system disease.

In an eighth aspect, the present invention provides the lamotrigine hydrate form A of the present invention or the composition of the present invention for use in treating a nervous system disease.

In some embodiments, the nervous system disease is selected from the group consisting of one or more of Alzheimer's disease, depression, multiple sclerosis, Parkinson's disease, and epilepsy.

In some embodiments, the medicament is used to treat the nervous system disease in combination with other medicaments.

In some embodiments, the medicament is in the form of a suspension.

In some embodiments, more than about 80% of lamotrigine in the medicament exists in a form of the lamotrigine hydrate form A.

Figure 1:
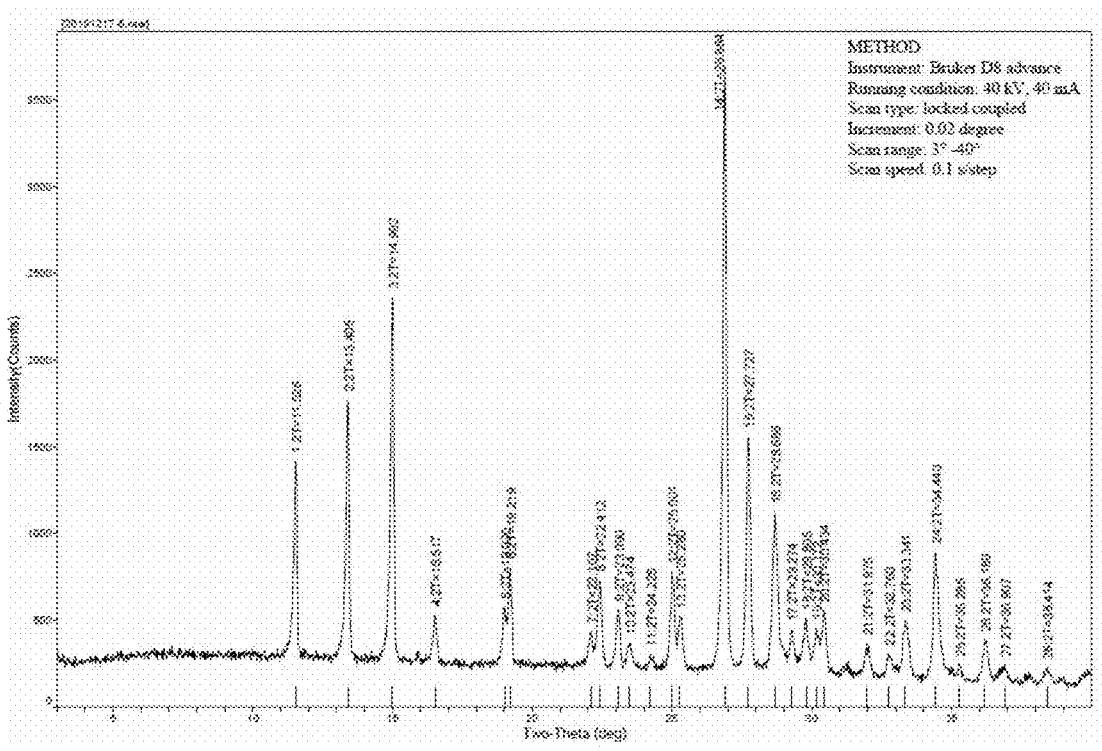
FIG. 1 shows an XRPD pattern of a lamotrigine hydrate form A.

A shows a microscopic photograph of a lamotrigine hydrate form A in Group 2 in Table 7;

B shows a microscopic photograph of a lamotrigine hydrate form A in Group 7 in Table 7; and C shows a microscopic photograph of a lamotrigine hydrate form A in Group 14 in Table.

DETAILED DESCRIPTION OF THE PREFERRED EMBODIMENTS

Unless otherwise defined, all technical and scientific terms used herein have the same meanings as those generally understood by those of ordinary skills in the art to which the present application belongs. In case of a contradiction, the definition provided in the present application shall prevail.

As used herein, the terms "comprise", "include", "have", "contain" or "relate to" and other variants thereof herein are inclusive or open-ended and do not exclude other elements or method steps that are not listed.

As used herein, the word "about" indicates a range within an acceptable standard error of a given value as appreciated by those of ordinary skills in the art, for example, ±0.05, ±0.1, ±0.2, ±0.3, ±0.5, ±1, ±2 or ±3, etc. As used herein, "about" refers to, for example, ±1%, ±2%, ±5% or ±10%.

As used herein, the term "amorphous" refers to any solid matter that is unordered in three dimensions. In some cases, an amorphous solid may be characterized by known techniques, including XRPD crystal diffraction analysis, solid-state nuclear magnetic resonance (ssNMR) spectroscopy, differential scanning calorimetry (DSC) or some combinations thereof. An XRPD pattern of an amorphous solid shows no obvious diffraction characteristic peak.

As used herein, the term "crystalline form" or "crystal" refers to any solid matter that exhibits a three-dimensional order, and that generates a characteristic XRPD pattern with well-defined peaks, as opposed to the amorphous solid matter.

As used herein, the term "XRPD pattern (x-ray powder diffraction pattern)" refers to a diffraction pattern observed by experiments, or parameters, data, or values derived therefrom. The XRPD pattern is typically characterized by peak position (abscissa) and/or peak intensity (ordinate).

As used herein, the term "2θ" refers to a peak position in degrees (°) set in an x-ray diffraction experiment, and typically refers to a unit of abscissa in the diffraction pattern. If a reflected beam is diffracted when an incident beam forms an angle θ with a lattice surface, the experiment needs to be set to record the reflected beam as an angle 2θ. It should be understood that a specific 2θ value of a specific crystalline form mentioned herein is intended to represent a 2θ value (expressed in degrees) measured by using the x-ray diffraction experimental conditions described herein. For example, as described herein, Cu-kα (Kα1 (Å): 1.540598 and Kα2 (Å): 1.544426) are used as radiation sources.

As used herein, the term "substantially the same" means that changes in representative peak positions and/or intensity are taken into consideration. For example, with respect to x-ray diffraction peaks, a person skilled in the art may understand that some variations in the peak position (2θ) may be shown, usually up to 0.1-0.2 degrees, and the instrument for measuring the diffraction may also bring some variations. In addition, a person skilled in the art may understand that changes in relative peak intensity may occur due to variations of instruments and factors such as crystallinity, preferred orientation, surface of the prepared sample, and other factors known to those skilled in the art, and therefore the relative peak intensity should only be regarded as a qualitative measurement.

As used herein, the term "low temperature" refers to a temperature lower than the normal temperature (about 25° C.).

As used herein, the term "suspension" refers to a solid medicament distributed in a liquid formulation in the form of particulate matters. As used herein, the term "dry suspension" refers to a powdery substance made from a solid medicament and thesuitable pharmaceutical excipients. When mixed with a solvent such as water, this powdery substance can be dispersed to form a suspension for oral use, for example. The lamotrigine dry suspension herein refers to a powdery substance containing lamotrigine particles. After the lamotrigine dry suspension is mixed with an aqueous phase to form a suspension, the lamotrigine particles are crystallized to form a lamotrigine hydrate form A. The terms "mixed suspension" and "suspension" are used interchangeably.

As used herein, the term "D90" refers to the fact that 90% of lamotrigine particles have a diameter less than the particle size as described.

As used herein, the term "lamotrigine hydrate form A" may also be referred to as "A crystalline form" or "crystalline form A". The lamotrigine hydrate form A is formed when lamotrigine particles are mixed with water.

As used herein, the term "microscopic particle size" refers to the "particle size of lamotrigine hydrate form A", which refers to the diameter of several lamotrigine hydrate forms A in the suspension observed and measured by a microscope after lamotrigine particles are mixed with water to form a suspension.

Crystalline Form

In an aspect, the present invention provides a lamotrigine hydrate form A, wherein an XRPD pattern of the lamotrigine hydrate form A includes characteristic peaks at diffraction angles (2θ) of about 11.5±0.2, 13.4±0.2, 15.0±0.2, 16.5±0.2, 19.2±0.2, 26.9±0.2, and 27.7±0.2 degrees, and has no characteristic peak(s) at one or more of diffraction angles (2θ) of about 15.9±0.2, 20.5±0.2, 23.5±0.2, 28.2±0.2, and 30.7±0.2 degrees.

In some embodiments, the XRPD pattern of the lamotrigine hydrate form A has no characteristic peak at a diffraction angle (2θ) of about 15.9±0.2 degrees. In some embodiments, the XRPD pattern of the lamotrigine hydrate form A has no characteristic peak at a diffraction angle (2θ) of about 30.7±0.2 degrees. In some embodiments, the XRPD pattern of the lamotrigine hydrate form A has no characteristic peaks at diffraction angles (2θ) of about 23.5±0.2, 28.2±0.2 and 30.7±0.2 degrees. In a preferred embodiment, the XRPD pattern of the lamotrigine hydrate form A has no characteristic peaks at diffraction angles 2θ of about 15.9±0.2, 20.5±0.2, 23.5±0.2, 28.2±0.2 and 30.7±0.2 degrees.

In some embodiments, the XRPD pattern of the lamotrigine hydrate form A comprises characteristic peaks at diffraction angles (2θ) substantially the same as diffraction angles shown in FIG. 1; or the XRPD pattern of the lamotrigine hydrate form A has XRPD peak positions substantially the same as XRPD peak positions shown in FIG. 1.

In the present application, the purity of the lamotrigine hydrate form A is determined by XRPD quantitative analysis. The XRPD quantitative analysis is based on the principle that the intensity of diffracted rays of each phase of a substance increases with the relative content of the phase in a mixture. A constant reference material is added to a tested powder sample to prepare a composite sample. The content of the phase to be tested is determined by measuring the ratio of the intensity of a diffracted ray of the phase to be tested in the composite sample to the intensity of a diffracted ray of an internal standard. $Al_2O_3$ is selected as the reference material.

In some embodiments, the lamotrigine hydrate form A has a purity of at least about 60%. In some embodiments, the lamotrigine hydrate form A has a purity of at least about 70%. In some embodiments, the purity of the lamotrigine hydrate form A is at least about 80%; preferably, the purity of the lamotrigine hydrate form A is at least about 90%; more preferably, the purity of the lamotrigine hydrate form A is at least about 95%; and most preferably, the lamotrigine hydrate form A is substantially pure. The "substantially pure" means that the form contains impurities of less than about 3% by weight, including other crystalline forms, solvated forms or amorphous forms.

Figure 2:
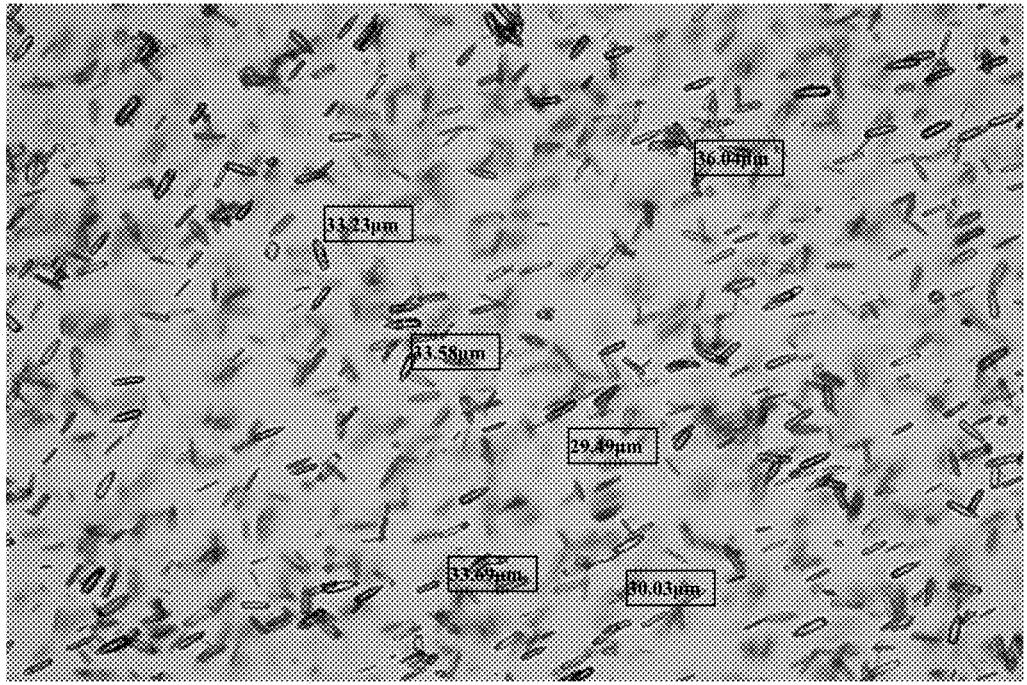
FIG. 2 shows a microscopic photograph of a lamotrigine hydrate form A.

The XRPD pattern of the lamotrigine hydrate form A with a purity of at least about 95% is shown in FIG. 1. The XRPD pattern of the lamotrigine hydrate form A with a purity of at least about 95% described above has a series of characteristic peaks at diffraction angles (2θ) of about 11.5±0.2, 13.4±0.2, 15.0±0.2, 16.5±0.2, 19.2±0.2, 26.9±0.2 and 27.7±0.2 degrees, and has no characteristic peak at diffraction angles (2θ) of about 15.9±0.2, 20.5±0.2, 23.5±0.2, 28.2±0.2 and 30.7±0.2 degrees. The lamotrigine hydrate form A with a purity of at least about 95% described above shows an appearance of short prism under a microscope, as shown in FIG. 2. It is shown in a thermogravimetric analysis on the lamotrigine hydrate form A with a purity of at least about 95% described above that with a weight loss of about 6.6% at 190° C., the lamotrigine hydrate form A is a monohydrate.

Preparation Method

In another aspect, the present invention provides a method for preparing a suspension comprising a lamotrigine hydrate form A, comprising the steps of: adding lamotrigine particles and a thickener to an aqueous phase; dispersing uniformly; and standing at a low temperature to obtain a suspension comprising the lamotrigine hydrate form A, wherein the lamotrigine particles have a particle size (D90) of about 1-30 μm.

In another aspect, the present invention provides a method for preparing a dry suspension comprising lamotrigine, comprising the steps of: mixing lamotrigine particles and a thickener, wherein the lamotrigine particles have a particle size (D90) of about 1-30 μm.

In another aspect, the present invention provides a method for preparing a lamotrigine hydrate form A, comprising filtering the suspension of the present invention, to obtain the lamotrigine hydrate form A. In some embodiments, the method may further comprise washing the crystals with water during the filtering to remove the thickener (or suspending agent) adhered to crystals.

In another aspect, the present invention provides a method for preparing a suspension of a lamotrigine hydrate form A, wherein the lamotrigine hydrate form A mataines the particles size within the range of 20-80 μm within at least one week, and has the antimicrobial stability of at least one month according to USP<51>. The method comprises the steps of:

(a) adding lamotrigine particles having a particle size (D90) of 1-30 μm, a pH modifier and a preservative to an aqueous phase; and (b) dispersing the lamotrigine particles, the pH modifier and the preservative in the aqueous phase uniformly; cooling the aqueous phase to a temperature of lower than about 25° C. to obtain a suspension comprising the lamotrigine hydrate form A.

In the present application, the stability of the lamotrigine hydrate form A, i.e., the stability of crystalline form and the stability of particle size, in the aqueous phase, is of great importance to the development of lamotrigine liquid formulations. The stability of crystalline form means that the crystalline form maintains consistent in the aqueous phase over a period of time. As dissolution rate varies between crystalline forms, resulting in significant differences in stability therefrom, the stability of crystal properties can be maintained by avoiding introduction of other crystalline forms, thereby ensuring safety and reliability of a product. The stability of particle size stability means that the particle size of the crystal in the aqueous phase is maintained within a certain range over a period of time. Excessive particle size may affect the uniform state of a drug and eventually lead to inaccurate dosing. In the present application, the stability of crystalline form and the stability of particle size of the lamotrigine hydrate form A in the suspension directly affects the stability and uniformity of the suspension. Excessive particle size of the crystalline form of the lamotrigine hydrate form A may lead to nonuniform content of active ingredients in the suspension due to obvious bulk crystals appearing in a solution, which eventually resulting in inaccurate dosing. Excessive increase amplitude of the crystalline form of the lamotrigine hydrate form A over a period of time also leads to obvious bulk crystals appearing in a solution, as well as short storage time of the suspension, making it difficult for actual application. Experience reveals that the particle size of the crystal exceeding 85 μm may easily result in a nonuniform system. In the present application, the effects of different preparation conditions on the stability of the crystalline form and particle size are investigated.

The suspension comprising the lamotrigine hydrate form A of the present invention also has the anti-microbial stability. As used herein, the term "anti-microbial stability" refers to the fact that a product has the anti-microbial stability when it meets the requirement for the anti-microbial effect according to USP<51>. According to the anti-microbial acceptance criteria (Class III product) of USP<51>, the suspension of the present invention needs to meet the following criteria:

Bacteria: on day 14, the log value of bacterial count decreased by not less than 1.0 as compared with the initial time point, and from Day 14 to Day 28, the log value of bacterial count does not increase; and Yeast and Mold: on Day 14 and Day 28, there is no increase with respect to the initial count.

Relevant test methods and requirements can be found in *Microbiological Tests/<51>Antimicrobial effctiveness testing* 53, Th eUnitd States Pharmacopoeia Convention, 2022 (https://online.uspnf.com/uspnf/document/1_GUID-772FE032-8921-4345-810E-945EF5BF1B15_3_en-US), the disclosure of which is incorporated herein by reference.

In some embodiments, the suspension comprising the lamotrigine hydrate form A or the lamotrigine hydrate form A is prepared by using lamotrigine particles having a particle size (D90) of about 1, 2, 4, 6, 8, 10, 12, 14, 15, 16, 18, 20, 25 or 30 μm. In some embodiments, the suspension comprising the lamotrigine hydrate form A or the lamotrigine hydrate form A is prepared by using lamotrigine particles having a particle size (D90) of about 1 μm. In some embodiments, the suspension comprising the lamotrigine hydrate form A or the lamotrigine hydrate form A is prepared by using lamotrigine particles having a particle size (D90) of about 15 μm. In some embodiments, the suspension comprising the lamotrigine hydrate form A or the lamotrigine hydrate form A is prepared by using lamotrigine particles having a particle size (D90) of about 30 μm. In a preferred embodiment, the lamotrigine particles have a particle size (D90) of about 8-12 μm. D90 means that particles having a particle size less than the mentioned particle size account for 90%.

In some embodiments, the particle size (D90) is selected from the group consisting of one or more of the following: about 4.5 μm, 4.6 μm, 4.7 μm, 4.8 μm, 4.9 μm, 5.3 μm, 5.1 μm, 5.2 μm, 5.3 μm, 5.4 μm, 5.5 μm, 5.6 μm, 5.7 μm, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, 7.0 μm, 7.1 μm, 7.2 μm, 7.3 μm, 7.4 μm, 7.5 μm, 7.6 μm, 7.7 μm, 7.8 μm, 7.9 μm and 8.0 μm, and a particle size (D90) range consisting of any two of the preceding particles sizes (D90).

In some embodiments, the particle size (D90) is selected from the group consisting of one or more of the following: about 2 μm, 12.1 μm, 12.2 μm, 12.3 μm, 12.4 μm, 12.5 μm, 12.6 μm, 12.7 μm, 12.8 μm, 12.9 μm and 13.0 μm, and a particle size (D90) range consisting of any two of the preceding particles sizes (D90).

In some embodiments, the particle size (D90) is selected from the group consisting of one or more of the following: about 8.0 µm, 8.1 µm, 8.2 µm, 8.3 µm, 8.4 µm, 8.5 µm, 8.6 µm, 8.7 µm, 8.8 µm, 8.9 µm, 9.0 µm, 9.1 µm, 9.2 µm, 9.3 µm, 9.4 µm, 9.5 µm, 9.6 µm, 9.7 µm, 9.8 µm, 9.9 µm, 10.0 µm, 10.1 µm, 10.2 µm, 10.3 µm, 10.4 µm, 10.5 µm, 10.6 µm, 10.7 µm, 10.8 µm, 10.9 µm, 11.0 µm, 11.1 µm, 11.2 µm, 11.3 µm, 11.4 µm, 11.5 µm, 11.6 µm, 11.7 µm, 11.8 µm, 11.9 µm and 12.0 µm, and a particle size (D90) range consisting of any two of the preceding particles sizes (D90).

In some embodiments, the suspension has a pH selected from the group consisting of one or more of the following: about 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH.

In some embodiments, the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pHs. In some embodiments, the suspension has a pH selected from the group consisting of one or more of the following: about 5.8, 5.9, 6.0, 6.1, 6.2, 6.3, 6.4, 6.5, 6.6, 6.7, 6.8, 6.85 and 6.9, and a pH range consisting of any two of the preceding pHs. In some embodiments, the suspension has a pH selected from the group consisting of one or more of the following: about 5.5, 5.6, 5.7, 5.8, 5.9, 6.0, 6.1, 6.2, 6.3, 6.4 and 6.5, and a pH range consisting of any two of the preceding pH.

In some embodiments, an appropriate pH modifier (in terms of type and/or content) is selected such that the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH.

In some embodiments, an appropriate pH modifier (in terms of type and/or content) is selected such that the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pHs. In some embodiments, an appropriate pH modifier (in terms of type and/or content) is selected such that the suspension has a pH selected from the group consisting of one or more of the following: about 5.8, 5.9, 6.0, 6.1, 6.2, 6.3, 6.4, 6.5, 6.6, 6.7, 6.8, 6.85 and 6.9, and a pH range consisting of any two of the preceding pH. In some embodiments, an appropriate pH modifier (in terms of type and/or content) is selected such that the suspension has a pH selected from the group consisting of one or more of the following: about 5.5, 5.6, 5.7, 5.8, 5.9, 6.0, 6.1, 6.2, 6.3, 6.4 and 6.5, and a pH range consisting of any two of the preceding pH.

In some embodiments, the particle size (D90) is in a range of about 6-14, 8-12, 8-10, 7-9, 8-9, 9-10, 10-11, 10-12, 11-12 or 11-13 µm. In some embodiments, an appropriate pH modifier (in terms of type and/or content) is selected such that the suspension has a pH in a range of: 4.0-7.0, 4.2-6.8, 4.4-6.8, 4.6-6.8, 4.6-6.6, 4.6-6.4, 4.6-6.2, 4.6-6.0, 4.6-5.8, 4.6-5.6, 4.6-5.4, 4.8-5.2, 5.0-6.8, 5.2-6.8, 5.4-6.8, 5.6-6.8, 5.8-6.8, 6.0-6.8, 6.0-6.6, 6.8-6.6, 5.8-6.6, 5.8-6.4, or 6.0-6.4. In some embodiments, the particle size (D90) is in a range of 8-10, 7-9, 7-8 or 8-9 µm, and meanwhile, an appropriate pH modifier (in terms of type and/or content) is selected such that the suspension has a pH in a range of: 4.6-6.8, 4.8-6.2, 4.8-6.0, 4.8-5.8 or 4.6-5.6. In some embodiments, the particle size (D90) is in a range of 10-12, 11-13, 11-12 or 12-13 µm, and meanwhile, an appropriate pH modifier (in terms of type and/or content) is selected such that the suspension has a pH in a range of: 5.6-6.8, 5.8-6.8, 5.8-6.6, 6.0-6.8, or 6.0-6.6.

In some embodiments, an appropriate particle size (D90) of the lamotrigine particles is selected to provide a range such that the lamotrigine hydrate form A in the suspension has the following increases in particle size: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

In some embodiments, an appropriate pH modifier (in terms of type and/or content) is selected to provide a range such that the lamotrigine hydrate form A in the suspension has the following increases in particle size: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

In some embodiments, the suspension comprising the lamotrigine hydrate form A has the anti-microbial stability lasting for at least one week, at least two weeks, at least three weeks, at least one month, at least two months or at least three months, according to the USP<51>.

In some embodiments, the acceptance criteria provided in the USP<51> are as follows:

Bacteria: on day 14, the log value of bacterial count decreased by not less than 1.0 as compared with the initial time point, and from Day 14 to Day 28, the log value of bacterial count does not increase; and Yeast and Mold: on Day 14 and Day 28, there is no increase with respect to the initial count.

In some embodiments, in the suspension comprising the lamotrigine hydrate form A and the dry suspension comprising lamotrigine according to the present invention, the preservative provides the anti-microbial stability lasting for at least one week, at least two weeks, at least three weeks, at least one month, at least two months or at least three months, following the acceptance criteria provided in the USP<51>; and optionally, the acceptance criteria provided in the USP<51> are as follows:

Bacteria: on day 14, the log value of bacterial count decreased by not less than 1.0 as compared with the initial time point, and from Day 14 to Day 28, the log value of bacterial count does not increase; and Yeast and Mold: on Day 14 and Day 28, there is no increase with respect to the initial count.

In some embodiments, the thickener (or suspending agent) is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations.

In a preferred embodiment, the thickener is selected from the group consisting of xanthan gum, povidone, colloidal microcrystalline cellulose, sodium alginate and their combinations. More preferably, the thickener is xanthan gum.

In some embodiments, based on about 10 parts by weight of the lamotrigine particles, the thickener is about 1-7 parts by weight, preferably, about 1-5 parts by weight.

In some embodiments, the weight ratio of the lamotrigine particles to the thickener is from about 1:1 to about 20:1, from about 1:1 to about 15:1, from about 1:1 to about 10:1, from about 2:1 to about 10:1, from about 5:1 to about 10:1, or from about 3:1 to about 10:1. In some embodiments, the weight ratio of the lamotrigine particles to the thickener is about 10:1, about 10:2, about 10:3, about 10:4, about 10:5, about 10:6, about 10:7, or about 10:8.

In some embodiments, based on about 10 parts by weight of the lamotrigine particles, the suspension comprising the lamotrigine hydrate form A, or the lamotrigine hydrate form A, is prepared by using about 2 parts by weight of xanthan gum. In some embodiments, based on about 10 parts by weight of the lamotrigine particles, the suspension comprising the lamotrigine hydrate form A, or the lamotrigine hydrate form A, is prepared by using about 3 parts by weight of xanthan gum. In some embodiments, based on about 10 parts by weight of the lamotrigine particles, the suspension comprising the lamotrigine hydrate form A, or the lamotrigine hydrate form A, is prepared by using about 4 parts by weight of xanthan gum. In some embodiments, based on about 10 parts by weight of the lamotrigine particles, the suspension comprising the lamotrigine hydrate form A, or the lamotrigine hydrate form A, is prepared by using about 6 parts by weight of xanthan gum. In some embodiments, based on about 10 parts by weight of the lamotrigine particles, the suspension comprising the lamotrigine hydrate form A, or the lamotrigine hydrate form A, is prepared by using about 7 parts by weight of xanthan gum.

In some embodiments, based on about 10 parts by weight of the lamotrigine particles, the suspension comprising the lamotrigine hydrate form A, or the lamotrigine hydrate form A, is prepared by using about 1-7 parts by weight of xanthan gum, preferably about 1-5 parts by weight of xanthan gum.

In some embodiments, the aqueous phase is purified water. In some embodiments, the aqueous phase may further comprise an additional solute such as an essence, a pH modifier, or a sweetener. In some embodiments, the aqueous phase comprises purified water and one or more of the following: an essence, a pH modifier and a sweetener.

In some embodiments, based on about 10 parts by weight of the lamotrigine particles, the aqueous phase is about 100-5000 parts by weight, preferably, about 500-2000 parts by weight.

In some embodiments, based on about 10 parts by weight of the lamotrigine particles, the suspension comprising the lamotrigine hydrate form A, or the lamotrigine hydrate form A, is prepared by using about 100, 200 or 300 parts by weight of purified water. In some embodiments, based on about 10 parts by weight of the lamotrigine particles, the suspension comprising the lamotrigine hydrate form A, or the lamotrigine hydrate form A, is prepared by using about 500, 600 or 800 parts by weight of purified water. In some embodiments, based on about 10 parts by weight of the lamotrigine particles, the suspension comprising the lamotrigine hydrate form A, or the lamotrigine hydrate form A, is prepared by using about 1000 or 2000 parts by weight of purified water. In some embodiments, based on about 10 parts by weight of the lamotrigine particles, the suspension comprising the lamotrigine hydrate form A, or the lamotrigine hydrate form A, is prepared by using about 2500 or 4000 parts by weight of purified water. In some embodiments, based on about 10 parts by weight of the lamotrigine particles, the suspension comprising the lamotrigine hydrate form A, or the lamotrigine hydrate form A, is prepared by using about 5000, 6000, 7000 or 8000 parts by weight of purified water.

In some embodiments, based on about 10 parts by weight of the lamotrigine particles, the suspension comprising the lamotrigine hydrate form A, or the lamotrigine hydrate form A, is prepared by using about 100-5000 parts by weight of purified water, preferably about 500-2000 parts by weight of purified water.

In some embodiments, the dispersing uniformly may be implemented by one or a combination of more of mechanical stirring, magnetic stirring, or manual shaking. The dispersing uniformly refers to the formation of a uniform system.

In some embodiments, the dispersing uniformly is achieved within about 1-120 minutes, preferably about 3-15 minutes. In some embodiments, the dispersing uniformly is achieved within about 1 minute, to obtain the suspension comprising the lamotrigine hydrate form A, or the lamotrigine hydrate form A. In some embodiments, the dispersing uniformly is achieved within about 2 minutes, to obtain the suspension comprising the lamotrigine hydrate form A, or the lamotrigine hydrate form A. In some embodiments, the dispersing uniformly is achieved within about 5 minutes, to obtain the suspension comprising the lamotrigine hydrate form A, or the lamotrigine hydrate form A. In some embodiments, the dispersing uniformly is achieved within about 10 minutes, to obtain the suspension comprising the lamotrigine hydrate form A, or the lamotrigine hydrate form A. In some embodiments, the dispersing uniformly is achieved within about 15 minutes, to obtain the suspension comprising the lamotrigine hydrate form A, or the lamotrigine hydrate form A. In some embodiments, the dispersing uniformly is achieved within about 20 minutes, to obtain the suspension comprising the lamotrigine hydrate form A, or the lamotrigine hydrate form A. In some embodiments, the dispersing uniformly is achieved within about 25 minutes, to obtain the suspension comprising the lamotrigine hydrate form A, or the lamotrigine hydrate form A. In some embodiments, the dispersing uniformly is achieved within about 30 minutes, to obtain the suspension comprising the lamotrigine hydrate form A, or the lamotrigine hydrate form A. In some embodiments, the dispersing uniformly is achieved within about 60 minutes, to obtain the suspension comprising the lamotrigine hydrate form A, or the lamotrigine hydrate form A. In some embodiments, the dispersing uniformly is achieved within about 120 minutes, to obtain the suspension comprising the lamotrigine hydrate form A, or the lamotrigine hydrate form A.

In some embodiments, the dispersing uniformly is implemented by mechanical stirring, magnetic stirring, and/or manual shaking for about 1-120 minutes, preferably 3-15 minutes.

In some embodiments, in order to save the preparation time, a specific dispersion time is not set, as long as uniform dispersion is achieved.

In some embodiments, the low temperature is selected from the group consisting of: not more than about −20° C., not more than about −10° C., not more than about −5° C., not more than about 0° C., not more than about 4° C., not more than about 10° C., not more than about 20° C., and not more than about 25° C. In some embodiments, the low temperature is selected from the group consisting of about −20° ° C. to about 25° C., from about −20° C. to about 20° C., from about −20° ° C. to about 0° C., from about 0° ° C. to about 20° C., from about 0° C. to about 4° C., and from about 4° C. to about 20° C.

In some embodiments, the low temperature is lower than about 25° C., preferably lower than about 20° C.

In some embodiments, the suspension comprising the lamotrigine hydrate form A, or the lamotrigine hydrate form A, is prepared at a low temperature of about −20° C. In some embodiments, the suspension comprising the lamotrigine hydrate form A, or the lamotrigine hydrate form A, is prepared at a low temperature of about −15° C. In some embodiments, the suspension comprising the lamotrigine hydrate form A, or the lamotrigine hydrate form A, is prepared at a low temperature of about −10° C. In some embodiments, the suspension comprising the lamotrigine hydrate form A, or the lamotrigine hydrate form A, is prepared at a low temperature of about −5° C. In some embodiments, the suspension comprising the lamotrigine hydrate form A, or the lamotrigine hydrate form A, is prepared at a low temperature of about 0° C. In some embodiments, the suspension comprising the lamotrigine hydrate form A, or the lamotrigine hydrate form A, is prepared at a low temperature of about 4° C. In some embodiments, the suspension comprising the lamotrigine hydrate form A, or the lamotrigine hydrate form A, is prepared at a low temperature of about 5° C. In some embodiments, the suspension comprising the lamotrigine hydrate form A, or the lamotrigine hydrate form A, is prepared at a low temperature of about 10° C. In some embodiments, the suspension comprising the lamotrigine hydrate form A, or the lamotrigine hydrate form A, is prepared at a low temperature of about 15° C. In some embodiments, the suspension comprising the lamotrigine hydrate form A, or the lamotrigine hydrate form A, is prepared at a low temperature of about 20° C.

In some embodiments, the standing at a low temperature is implemented for at least about 30 minutes, preferably at least about 2 hours.

In some embodiments, the standing at a low temperature is implemented for about 30 minutes, to prepare the suspension comprising the lamotrigine hydrate form A, or the lamotrigine hydrate form A. In some embodiments, the standing at a low temperature is implemented for about 1 hour, to prepare the suspension comprising the lamotrigine hydrate form A, or the lamotrigine hydrate form A. In some embodiments, the standing at a low temperature is implemented for about 2 hours, to prepare the suspension comprising the lamotrigine hydrate form A, or the lamotrigine hydrate form A. In some embodiments, the standing at a low temperature is implemented for about 8 hours, to prepare the suspension comprising the lamotrigine hydrate form A, or the lamotrigine hydrate form A. In some embodiments, the standing at a low temperature is implemented for about 24 hours, to prepare the suspension comprising the lamotrigine hydrate form A, or the lamotrigine hydrate form A.

In some embodiments, the standing at a low temperature is implemented in a time interval after the dispersing uniformly.

In some embodiments, the time interval between the dispersing uniformly and the standing at a low temperature is at most about 12 hours, preferably at most about 1 minute, more preferably 0.

In some embodiments, the suspension comprising the lamotrigine hydrate form A, or the lamotrigine hydrate form A, is prepared with a time interval of not more than about 12 hours between the dispersing uniformly and the standing at a low temperature. In some embodiments, the suspension comprising the lamotrigine hydrate form A, or the lamotrigine hydrate form A, is prepared with a time interval of not more than about 8 hours. In some embodiments, the suspension comprising the lamotrigine hydrate form A, or the lamotrigine hydrate form A, is prepared with a time interval of not more than about 2 hours. In some embodiments, the suspension comprising the lamotrigine hydrate form A, or the lamotrigine hydrate form A, is prepared with a time interval of not more than about 60 minutes. In some embodiments, the suspension comprising the lamotrigine hydrate form A, or the lamotrigine hydrate form A, is prepared with a time interval of not more than about 30 minutes. In some embodiments, the suspension comprising the lamotrigine hydrate form A, or the lamotrigine hydrate form A, is prepared with a time interval of not more than about 20 minutes. In some embodiments, the suspension comprising the lamotrigine hydrate form A, or the lamotrigine hydrate form A, is prepared with a time interval of not more than about 10 minutes. In some embodiments, the suspension comprising the lamotrigine hydrate form A, or the lamotrigine hydrate form A, is prepared with a time interval of not more than about 1 minute. In some embodiments, the suspension comprising the lamotrigine hydrate form A, or the lamotrigine hydrate form A, is prepared with a time interval of 0.

In some embodiments, in order to save the preparation time, subsequent steps are performed directly after completion of the previous step without setting a time interval.

In some embodiments, a method for preparing a suspension comprising a lamotrigine hydrate form A comprises the steps of: adding about 10 parts by weight of lamotrigine particles having a particle size (D90) of about 1-30 μm and about 1-7 parts by weight of thickeners to about 100-5000 parts by weight of an aqueous phase; dispersing uniformly; and standing at a low temperature of 25° C. for at least 30 minutes, to obtain the suspension comprising the lamotrigine hydrate form A. In a specific embodiment, the method for preparing the suspension comprising the lamotrigine hydrate form A comprises the steps of: adding about 10 parts by weight of lamotrigine particles having a particle size (D90) of about 8-12 μm and about 1-5 parts by weight of xanthan gum into about 500-2000 parts by weight of purified water; dispersing uniformly; and standing at a low temperature of 20° C. for at least 2 hours, to obtain the suspension comprising the lamotrigine hydrate form A.

In some embodiments, the suspension may be applied as a suspension. The suspension prepared by the method of the present invention may be directly used as a suspension.

In some embodiments, further included is preparing lamotrigine particles and a thickener together with one or more of a filler, a sweetener, a pH modifier and a preservative into a dry suspension, which is then added to the aqueous phase.

In a preferred embodiment, the dry suspension is prepared by direct mixing.

In some embodiments, the filler is one or a combination of more of mannitol, microcrystalline cellulose, sucrose, and lactose, and based on about 10 parts by weight of the lamotrigine particles, the filler is about 20-60 parts by weight; the sweetener is one or a combination of more of sucralose, aspartame, and sodium saccharin, and based on about 10 parts by weight of the lamotrigine particles, the sweetener is about 1-3 parts by weight; the pH modifier is one or a combination of more of disodium hydrogen phosphate, citric acid and sodium citrate, and based on about 10 parts by weight of the lamotrigine particles, the pH modifier is about 2-5 parts by weight; and the preservative is one or a combination of more of sodium propylparaben, sodium methylparaben, sodium benzoate, and potassium sorbate, and based on about 10 parts by weight of the lamotrigine particles, the preservative is about 1-3 parts by weight.

In some embodiments, the pH modifier is one or a combination of more of sodium dihydrogen phosphate, disodium hydrogen phosphate, citric acid, and sodium citrate. In some embodiments, the pH modifier is one or a combination of more of sodium dihydrogen phosphate, disodium hydrogen phosphate, and citric acid. In some embodiments, the pH modifier is one or a combination of more of sodium dihydrogen phosphate and citric acid. In some embodiments, the pH modifier is one or a combination of more of disodium hydrogen phosphate and citric acid. In some embodiments, the pH modifier is one or a combination of more of sodium dihydrogen phosphate and disodium hydrogen phosphate. In some embodiments, the pH modifier is sodium dihydrogen phosphate, disodium hydrogen phosphate, citric acid, or sodium citrate.

In some embodiments, based on about 10 parts by weight of the lamotrigine particles, the pH modifier has an amount selected from the group consisting of one or more of the following: about 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight, 2.5 parts by weight, 2.6 parts by weight, 2.7 parts by weight, 2.8 parts by weight, 2.9 parts by weight, 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, based on about 10 parts by weight of the lamotrigine particles, the pH modifier has an amount selected from the group consisting of one or more of the following: about 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight, 2.5 parts by weight, 2.6 parts by weight, 2.7 parts by weight, 2.8 parts by weight, 2.9 parts by weight, 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight and 5.1 parts by weight, and a range consisting of any two of the previous amounts.

In some embodiments, based on about 10 parts by weight of the lamotrigine particles, the pH modifier has an amount selected from the group consisting of one or more of the following: about 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, the pH modifier is a combination of disodium hydrogen phosphate and critic acid, and based on about 10 parts by weight of the lamotrigine particles, the total amount of the disodium hydrogen phosphate and the critic acid is selected from the group consisting of one or more of the following: about 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, the pH modifier is critic acid, and based on about 10 parts by weight of the lamotrigine particles, the critic acid has an amount selected from the group consisting of one or more of the following: about 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight and 2.5 parts by weight, and a range consisting of any two of the previous amounts.

In some embodiments, the pH modifier is sodium dihydrogen phosphate, and based on about 10 parts by weight of the lamotrigine particles, the sodium dihydrogen phosphate has an mount of about 3 parts by weight.

In some embodiments, more than about 60% of lamotrigine exists in a form of the lamotrigine hydrate form A. In some embodiments, more than about 70% of lamotrigine exists in a form of the lamotrigine hydrate form A. In some embodiments, more than about 80% of lamotrigine exists in a form of the lamotrigine hydrate form A; preferably, more than about 90% of lamotrigine exists in a form of the lamotrigine hydrate form A; more preferably, more than about 95% of lamotrigine exists in a form of the lamotrigine hydrate form A; and most preferably, more than about 97% of lamotrigine exists in a form of the lamotrigine hydrate form A.

In another aspect, the present invention provides a method for reconstituting a composition comprising lamotrigine particles and a thickener to form a suspension comprising a lamotrigine hydrate form A immediately before use. In this method, same processes, required components and amounts as those in the method for preparing a suspension comprising a lamotrigine hydrate form A described above may be used. This method may comprise the steps of: adding the composition comprising the lamotrigine particles and the thickener to an aqueous phase; dispersing uniformly; and standing at low temperature, to obtain the suspension comprising the lamotrigine hydrate form A, where the lamotrigine particles have a particle size (D90) of about 1-30 μm.

In some embodiments, the composition comprising the lamotrigine particles and the thickener is reconstituted by using lamotrigine particles having a particle size (D90) of about 1 μm, to obtain the suspension comprising the lamotrigine hydrate form A. In some embodiments, the composition comprising the lamotrigine particles and the thickener is reconstituted by using lamotrigine particles having a particle size (D90) of about 8 μm, to obtain the suspension comprising the lamotrigine hydrate form A. In some embodiments, the composition comprising the lamotrigine particles and the thickener is reconstituted by using lamotrigine particles having a particle size (D90) of about 12 μm, to obtain the suspension comprising the lamotrigine hydrate form A. In some embodiments, the composition comprising the lamotrigine particles and the thickener is reconstituted by using lamotrigine particles having a particle size (D90) of about 30 μm, to obtain the suspension comprising the lamotrigine hydrate form A.

In a preferred embodiment, the lamotrigine particles have a particle size (D90) of about 8-12 μm.

In some embodiments, the lamotrigine hydrate form A in the suspension of the present invention has a particle size selected from the group consisting of the following one or more ranges: about 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm.

In some embodiments, after standing at 4° C. for 24 hours, standing at the normal temperature for 1 day, standing at the normal temperature for 3 days, standing at the normal temperature for 6 days, standing at the normal temperature for 10 days, standing at the normal temperature for 15 days, and standing at the normal temperature for 1 month, the lamotrigine hydrate form A in the suspension of the present invention has a particle size selected from the group consisting of the following one or more ranges: about 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm.

In some embodiments, the thickener (or suspending agent) in the composition comprising the lamotrigine particles and the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations.

In a preferred embodiment, the thickener is selected from the group consisting of xanthan gum, povidone, colloidal microcrystalline cellulose, sodium alginate and their combinations. More preferably, the thickener is xanthan gum.

In some embodiments, based on about 10 parts by weight of the lamotrigine particles, the thickener is about 1-7 parts by weight, preferably, about 1-5 parts by weight.

In some embodiments, in the composition comprising the lamotrigine particles and the thickener, the suspension comprising the lamotrigine hydrate form A is obtained by reconstituting the above composition comprising about 2 parts by weight of xanthan gum, based on about 10 parts by weight of the lamotrigine particles; in some embodiments, the suspension comprising the lamotrigine hydrate form A is obtained by reconstituting the above composition comprising about 3 parts by weight of xanthan gum, based on about 10 parts by weight of the lamotrigine particles; in some embodiments, the suspension comprising the lamotrigine hydrate form A is obtained by reconstituting the above composition comprising about 4 parts by weight of xanthan gum, based on about 10 parts by weight of the lamotrigine particles; in some embodiments, the suspension comprising the lamotrigine hydrate form A is obtained by reconstituting the above composition comprising about 6 parts by weight of xanthan gum, based on about 10 parts by weight of the lamotrigine particles; and in some embodiments, the suspension comprising the lamotrigine hydrate form A is obtained by reconstituting the above composition comprising about 7 parts by weight of xanthan gum, based on about 10 parts by weight of the lamotrigine particles.

In some embodiments, in the composition comprising the lamotrigine particles and the thickener, the suspension comprising the lamotrigine hydrate form A is obtained by reconstituting the above composition comprising about 1-5 parts by weight of xanthan gum, based on 10 parts by weight of the lamotrigine particles.

In some embodiments, the composition comprising the lamotrigine particles and the thickener may further comprise one or more of a filler, a sweetener, a pH modifier and a preservative.

In some embodiments, the aqueous phase is purified water. In some embodiments, the aqueous phase may further comprise an additional solute such as an essence, a pH modifier, or a sweetener. In some embodiments, the aqueous phase comprises purified water and one or more of the following: an essence, a pH modifier and a sweetener.

In some embodiments, based on about 10 parts by weight of the lamotrigine particles, the aqueous phase is about 100-5000 parts by weight, preferably, about 500-2000 parts by weight.

In some embodiments, based on about 10 parts by weight of the lamotrigine particles, the suspension comprising the lamotrigine hydrate form A is obtained by reconstituting by using about 100 parts by weight of purified water. In some embodiments, based on about 10 parts by weight of the lamotrigine particles, the suspension comprising the lamotrigine hydrate form A is obtained by reconstituting by using about 500 parts by weight of purified water. In some embodiments, based on about 10 parts by weight of the lamotrigine particles, the suspension comprising the lamotrigine hydrate form A is obtained by reconstituting by using about 1000 parts by weight of purified water. In some embodiments, based on about 10 parts by weight of the lamotrigine particles, the suspension comprising the lamotrigine hydrate form A is obtained by reconstituting by using about 2500 parts by weight of purified water. In some embodiments, based on about 10 parts by weight of lamotrigine, the suspension comprising the lamotrigine hydrate form A is obtained by reconstituting by using about 5000 parts by weight of purified water.

In some embodiments, based on about 10 parts by weight of the lamotrigine particles, a stable suspension comprising the lamotrigine hydrate form A may be obtained by reconstituting by using about 100-5000 parts by weight of purified water, preferably about 500-2000 parts by weight of purified water.

In some embodiments, the dispersing uniformly may be implemented by one or a combination of more of mechanical stirring, magnetic stirring, or manual shaking.

In some embodiments, the dispersing uniformly is achieved within about 1-120 minutes, preferably about 3-15 minutes. In some embodiments, the dispersing uniformly is achieved within about 1 minute, to obtain the suspension comprising the lamotrigine hydrate form A by reconstitution. In some embodiments, the dispersing uniformly is achieved within about 2 minutes, to obtain the suspension comprising the lamotrigine hydrate form A by reconstitution. In some embodiments, the dispersing uniformly is achieved within about 5 minutes, to obtain the suspension comprising the lamotrigine hydrate form A by reconstitution. In some embodiments, the dispersing uniformly is achieved within about 10 minutes, to obtain the suspension comprising the lamotrigine hydrate form A by reconstitution. In some embodiments, the dispersing uniformly is achieved within about 15 minutes, to obtain the suspension comprising the lamotrigine hydrate form A by reconstitution. In some embodiments, the dispersing uniformly is achieved within about 20 minutes, to obtain the suspension comprising the lamotrigine hydrate form A by reconstitution. In some embodiments, the dispersing uniformly is achieved within about 25 minutes, to obtain the suspension comprising the lamotrigine hydrate form A by reconstitution. In some embodiments, the dispersing uniformly is achieved within about 30 minutes, to obtain the suspension comprising the lamotrigine hydrate form A by reconstitution. In some embodiments, the dispersing uniformly is achieved within about 60 minutes, to obtain the suspension comprising the lamotrigine hydrate form A by reconstitution. In some embodiments, the dispersing uniformly is achieved within about 120 minutes, to obtain the suspension comprising the lamotrigine hydrate form A by reconstitution.

In some embodiments, the dispersing uniformly is implemented by mechanical stirring, magnetic stirring, and/or manual shaking for about 1-120 minutes, preferably 3-15 minutes.

In some embodiments, in order to save the preparation time, a specific dispersion time is not set, as long as uniform dispersion is achieved.

In some embodiments, the low temperature is lower than about 25° C., preferably lower than about 20° ° C.

In some embodiments, the low temperature is about −20° C., to obtain the suspension comprising the lamotrigine hydrate form A by reconstitution. In some embodiments, the low temperature is about −15° C., to obtain the suspension comprising the lamotrigine hydrate form A by reconstitution. In some embodiments, the low temperature is about −10° C., to obtain the suspension comprising the lamotrigine hydrate form A by reconstitution. In some embodiments, the low temperature is about −5° C., to obtain the suspension comprising the lamotrigine hydrate form A by reconstitution. In some embodiments, the low temperature is about 0° C., to obtain the suspension comprising the lamotrigine hydrate form A by reconstitution. In some embodiments, the low temperature is about 4° C., to obtain the suspension comprising the lamotrigine hydrate form A by reconstitution. In some embodiments, the low temperature is about 5° C., to obtain the suspension comprising the lamotrigine hydrate form A by reconstitution. In some embodiments, the low temperature is about 10° C., to obtain the suspension comprising the lamotrigine hydrate form A by reconstitution. In some embodiments, the low temperature is about 15° C., to obtain the suspension comprising the lamotrigine hydrate form A by reconstitution. In some embodiments, the low temperature is about 20° C., to obtain the suspension comprising the lamotrigine hydrate form A by reconstitution.

In some embodiments, the standing at a low temperature is implemented for at least about 30 minutes, preferably at least about 2 hours.

In some embodiments, the standing at a low temperature is implemented for at least about 24 hours, to obtain the suspension comprising the lamotrigine hydrate form A by reconstitution. In some embodiments, the standing at a low temperature is implemented for at least about 8 hours, to obtain the suspension comprising the lamotrigine hydrate form A by reconstitution. In some embodiments, the standing at a low temperature is implemented for at least about 2 hours, to obtain the suspension comprising the lamotrigine hydrate form A by reconstitution. In some embodiments, the standing at a low temperature is implemented for at least about 1 hours, to obtain the suspension comprising the lamotrigine hydrate form A by reconstitution. In some embodiments, the standing at a low temperature is implemented for at least about 30 minutes, to obtain the suspension comprising the lamotrigine hydrate form A by reconstitution.

In some embodiments, the standing at a low temperature is implemented in a time interval after the dispersing uniformly.

In some embodiments, the time interval between the dispersing uniformly and the standing at a low temperature is at most about 12 hours, preferably at most about 1 minute, more preferably 0.

In some embodiments, the suspension comprising the lamotrigine hydrate form A is obtained by reconstitution with a time interval of about 12 hours between the dispersing uniformly and the standing at a low temperature. In some embodiments, the suspension comprising the lamotrigine hydrate form A is obtained by reconstitution with a time interval of about 8 hours. In some embodiments, the suspension comprising the lamotrigine hydrate form A is obtained by reconstitution with a time interval of about 2 hours. In some embodiments, the suspension comprising the lamotrigine hydrate form A is obtained by reconstitution with a time interval of about 30 minutes. In some embodiments, the suspension comprising the lamotrigine hydrate form A is obtained by reconstitution with a time interval of about 20 minutes. In some embodiments, the suspension comprising the lamotrigine hydrate form A is obtained by reconstitution with a time interval of about 10 minutes. In some embodiments, the suspension comprising the lamotrigine hydrate form A is obtained by reconstitution with a time interval of about 1 minute. In some embodiments, the suspension comprising the lamotrigine hydrate form A is obtained by reconstitution with a time interval of 0.

In some embodiments, in order to save the preparation time, subsequent steps are performed directly after completion of the previous step without setting a time interval.

Dry Lamotrigine Suspension and Lamotrigine Suspension

In another aspect, the present invention provides a dry lamotrigine suspension, comprising a therapeutically effective amount of lamotrigine particles and one or more pharmaceutically acceptable excipients, where the lamotrigine particles have a particle size (D90) of about 1-30 μm.

In some embodiments, when the dry lamotrigine suspension is mixed with an aqueous phase, more than about 80%, 85%, 90% and 95% of lamotrigine exists in a form of a lamotrigine hydrate form A.

In some embodiments, when the dry lamotrigine suspension is mixed with an aqueous phase, the obtained suspension has a pH of about 4.6-6.9.

In another aspect, the present invention provides a lamotrigine suspension, comprising a therapeutically effective amount of a lamotrigine hydrate form A and one or more pharmaceutically acceptable excipients, where the lamotrigine hydrate form A has a particle size of about 20-80 μm.

In some embodiments, an XRPD pattern of the lamotrigine hydrate form A comprises characteristic peaks at diffraction angles (2θ) of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles (2θ) of about 15.9±0.2, 20.5±0.2, 23.5±0.2, 28.2±0.2, and 30.7±0.2 degrees; and optionally, the XRPD pattern of the lamotrigine hydrate form A has no characteristic peak at diffraction angles (2θ) of about 15.9±0.2, 20.5±0.2, 23.5±0.2, 28.2±0.2 and 30.7±0.2 degrees.

In some embodiments, the XRPD pattern of the lamotrigine hydrate form A comprises characteristic peaks at diffraction angles 2θ substantially the same as diffraction angles shown in FIG. 1.

In some embodiments, the XRPD pattern of the lamotrigine hydrate form A has XRPD peak positions substantially the same as those shown in FIG. 1. In some embodiments, the XRPD pattern of the lamotrigine hydrate form A has XRPD peak positions the same as those shown in FIG. 1.

In some embodiments, the particle size (D90) is selected from the group consisting of one or more of the following: about 4.5 μm, 4.6 μm, 4.7 μm, 4.8 μm, 4.9 μm, 5.3 μm, 5.1 μm, 5.2 μm, 5.3 μm, 5.4 μm, 5.5 μm, 5.6 μm, 5.7 μm, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, 7.0 μm, 7.1 μm, 7.2 μm, 7.3 μm, 7.4 μm, 7.5 μm, 7.6 μm, 7.7 μm, 7.8 μm, 7.9 μm and 8.0 μm, and a particle size (D90) range consisting of any two of the preceding particles sizes (D90).

In some embodiments, the particle size (D90) is selected from the group consisting of one or more of the following: about 12 μm, 12.1 μm, 12.2 μm, 12.3 μm, 12.4 μm, 12.5 μm, 12.6 μm, 12.7 μm, 12.8 μm, 12.9 μm and 13.0 μm, and a particle size (D90) range consisting of any two of the preceding particles sizes (D90).

In some embodiments, the particle size (D90) is selected from the group consisting of one or more of the following: about 8.0 μm, 8.1 μm, 8.2 μm, 8.3 μm, 8.4 μm, 8.5 μm, 8.6 μm, 8.7 μm, 8.8 μm, 8.9 μm, 9.0 μm, 9.1 μm, 9.2 μm, 9.3 μm, 9.4 μm, 9.5 μm, 9.6 μm, 9.7 μm, 9.8 μm, 9.9 μm, 10.0 μm, 10.1 μm, 10.2 μm, 10.3 μm, 10.4 μm, 10.5 μm, 10.6 μm, 10.7 μm, 10.8 μm, 10.9 μm, 11.0 μm, 11.1 μm, 11.2 μm, 11.3 μm, 11.4 μm, 11.5 μm, 11.6 μm, 11.7 μm, 11.8 μm, 11.9 μm and 12.0 μm, and a particle size (D90) range consisting of any two of the preceding particles sizes (D90).

In some embodiments, the suspension has a pH selected from the group consisting of one or more of the following: about 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pHs.

In some embodiments, the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH. In some embodiments, the suspension has a pH selected from the group consisting of one or more of the following: about 5.8, 5.9, 6.0, 6.1, 6.2, 6.3, 6.4, 6.5, 6.6, 6.7, 6.8, 6.85 and 6.9, and a pH range consisting of any two of the preceding pHs. In some embodiments, the suspension has a pH selected from the group consisting of one or more of the following: about 5.5, 5.6, 5.7, 5.8, 5.9, 6.0, 6.1, 6.2, 6.3, 6.4 and 6.5, and a pH range consisting of any two of the preceding pH.

In some embodiments, an appropriate pH modifier (in terms of type and/or content) is selected such that the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pHs.

In some embodiments, an appropriate pH modifier (in terms of type and/or content) is selected such that the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pHs. In some embodiments, an appropriate pH modifier (in terms of type and/or content) is selected such that the suspension has a pH selected from the group consisting of one or more of the following: about 5.8, 5.9, 6.0, 6.1, 6.2, 6.3, 6.4, 6.5, 6.6, 6.7, 6.8, 6.85 and 6.9, and a pH range consisting of any two of the preceding pH. In some embodiments, an appropriate pH modifier (in terms of type and/or content) is selected such that the suspension has a pH selected from the group consisting of one or more of the following: about 5.5, 5.6, 5.7, 5.8, 5.9, 6.0, 6.1, 6.2, 6.3, 6.4 and 6.5, and a pH range consisting of any two of the preceding pH.

In some embodiments, the particle size (D90) is in a range of about 6-14, 8-12, 8-10, 7-9, 8-9, 9-10, 10-11, 10-12, 11-12 or 11-13 μm. In some embodiments, an appropriate pH modifier (in terms of type and/or content) is selected such that the suspension has a pH in a range of: 4.0-7.0, 4.2-6.8, 4.4-6.8, 4.6-6.8, 4.6-6.6, 4.6-6.4, 4.6-6.2, 4.6-6.0, 4.6-5.8, 4.6-5.6, 4.6-5.4, 4.8-5.2, 5.0-6.8, 5.2-6.8, 5.4-6.8, 5.6-6.8, 5.8-6.8, 6.0-6.8, 6.0-6.6, 6.8-6.6, 5.8-6.6, 5.8-6.4, or 6.0-6.4. In some embodiments, the particle size (D90) is in a range of 8-10, 7-9, 7-8 or 8-9 μm, and meanwhile, an appropriate pH modifier (in terms of type and/or content) is selected such that the suspension has a pH in a range of: 4.6-6.8, 4.8-6.2, 4.8-6.0, 4.8-5.8 or 4.6-5.6. In some embodiments, the particle size (D90) is in a range of 10-12, 11-13, 11-12 or 12-13 μm, and meanwhile, an appropriate pH modifier (in terms of type and/or content) is selected such that the suspension has a pH in a range of: 5.6-6.8, 5.8-6.8, 5.8-6.6, 6.0-6.8, or 6.0-6.6.

In some embodiments, an appropriate pH modifier (in terms of type and/or content) is selected to provide a range such that the lamotrigine hydrate form A has the following increases in particle size: the particle size increased by less than 30%, less than 20%, less than 10% or less than 5% in the range of about Day 1, about Day 2, about Day 3, about Day 5, about Week 1, about Week 2, about Week 3, about Week 4, about Week 6 or about Week 8.

In some embodiments, the thickener (or suspending agent) is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations.

In a preferred embodiment, the thickener is selected from the group consisting of xanthan gum, povidone, colloidal microcrystalline cellulose, sodium alginate and their combinations. More preferably, the thickener is xanthan gum.

In some embodiments, based on about 10 parts by weight of the lamotrigine particles, the thickener is about 1-7 parts by weight, preferably, about 1-5 parts by weight.

In some embodiments, the weight ratio of the lamotrigine particles to the thickener is from about 1:1 to about 20:1, from about 1:1 to about 15:1, from about 1:1 to about 10:1, from about 2:1 to about 10:1, from about 5:1 to about 10:1, or from about 3:1 to about 10:1. In some embodiments, the weight ratio of the lamotrigine particles to the thickener is about 10:1, about 10:2, about 10:3, about 10:4, about 10:5, about 10:6, about 10:7, or about 10:8.

In some embodiments, based on about 10 parts by weight of the lamotrigine particles, the suspension comprising the lamotrigine hydrate form A, or the lamotrigine hydrate form A, is prepared by using about 2 parts by weight of xanthan gum. In some embodiments, based on about 10 parts by weight of the lamotrigine particles, the suspension comprising the lamotrigine hydrate form A, or the lamotrigine hydrate form A, is prepared by using about 3 parts by weight of xanthan gum. In some embodiments, based on about 10 parts by weight of the lamotrigine particles, the suspension comprising the lamotrigine hydrate form A, or the lamotrigine hydrate form A, is prepared by using about 4 parts by weight of xanthan gum. In some embodiments, based on about 10 parts by weight of the lamotrigine particles, the suspension comprising the lamotrigine hydrate form A, or the lamotrigine hydrate form A, is prepared by using about 6 parts by weight of xanthan gum. In some embodiments, based on about 10 parts by weight of the lamotrigine particles, the suspension comprising the lamotrigine hydrate form A, or the lamotrigine hydrate form A, is prepared by using about 7 parts by weight of xanthan gum.

In some embodiments, based on about 10 parts by weight of the lamotrigine particles, the suspension comprising the lamotrigine hydrate form A, or the lamotrigine hydrate form A, is prepared by using about 1-7 parts by weight of xanthan gum, preferably about 1-5 parts by weight of xanthan gum.

In some embodiments, the aqueous phase is purified water. In some embodiments, the aqueous phase may further comprise an additional solute such as an essence, a pH modifier, or a sweetener. In some embodiments, the aqueous phase comprises purified water and one or more of the following: an essence, a pH modifier and a sweetener.

In some embodiments, based on about 10 parts by weight of the lamotrigine particles, the aqueous phase is about 100-5000 parts by weight, preferably, about 500-2000 parts by weight.

In some embodiments, based on about 10 parts by weight of the lamotrigine particles, the suspension comprising the lamotrigine hydrate form A, or the lamotrigine hydrate form A, is prepared by using about 100, 200 or 300 parts by weight of purified water. In some embodiments, based on about 10 parts by weight of the lamotrigine particles, the suspension comprising the lamotrigine hydrate form A, or the lamotrigine hydrate form A, is prepared by using about 500, 600 or 800 parts by weight of purified water. In some embodiments, based on about 10 parts by weight of the lamotrigine particles, the suspension comprising the lamotrigine hydrate form A, or the lamotrigine hydrate form A, is prepared by using about 1000 or 2000 parts by weight of purified water. In some embodiments, based on about 10 parts by weight of the lamotrigine particles, the suspension comprising the lamotrigine hydrate form A, or the lamotrigine hydrate form A, is prepared by using about 2500 or 4000 parts by weight of purified water. In some embodiments, based on about 10 parts by weight of the lamotrigine particles, the suspension comprising the lamotrigine hydrate form A, or the lamotrigine hydrate form A, is prepared by using about 5000, 6000, 7000 or 8000 parts by weight of purified water.

In some embodiments, based on about 10 parts by weight of the lamotrigine particles, the suspension comprising the lamotrigine hydrate form A, or the lamotrigine hydrate form A, is prepared by using about 100-5000 parts by weight of purified water, preferably about 500-2000 parts by weight of purified water.

In some embodiments, the filler is one or a combination of more of mannitol, microcrystalline cellulose, sucrose, and lactose, and based on about 10 parts by weight of the lamotrigine particles, the filler is about 20-60 parts by weight; the sweetener is one or a combination of more of sucralose, aspartame, and sodium saccharin, and based on about 10 parts by weight of the lamotrigine particles, the sweetener is about 1-3 parts by weight; the pH modifier is one or a combination of more of disodium hydrogen phosphate, citric acid and sodium citrate, and based on about 10 parts by weight of the lamotrigine particles, the pH modifier is about 2-5 parts by weight; and the preservative is one or a combination of more of sodium propylparaben, sodium methylparaben, sodium benzoate, and potassium sorbate, and based on about 10 parts by weight of the lamotrigine particles, the preservative is about 1-3 parts by weight.

In some embodiments, the pH modifier is one or a combination of more of sodium dihydrogen phosphate, disodium hydrogen phosphate, citric acid, and sodium citrate. In some embodiments, the pH modifier is one or a combination of more of sodium dihydrogen phosphate, disodium hydrogen phosphate, and citric acid. In some embodiments, the pH modifier is one or a combination of more of sodium dihydrogen phosphate and citric acid. In some embodiments, the pH modifier is one or a combination of more of disodium hydrogen phosphate and citric acid. In some embodiments, the pH modifier is one or a combination of more of sodium dihydrogen phosphate and disodium hydrogen phosphate. In some embodiments, the pH modifier is sodium dihydrogen phosphate, disodium hydrogen phosphate, citric acid, or sodium citrate.

In some embodiments, based on about 10 parts by weight of the lamotrigine particles, the pH modifier has an amount selected from the group consisting of one or more of the following: about 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight, 2.5 parts by weight, 2.6 parts by weight, 2.7 parts by weight, 2.8 parts by weight, 2.9 parts by weight, 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, based on about 10 parts by weight of the lamotrigine particles, the pH modifier has an amount selected from the group consisting of one or more of the following: 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight, 2.5 parts by weight, 2.6 parts by weight, 2.7 parts by weight, 2.8 parts by weight, 2.9 parts by weight, 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight and 5.1 parts by weight, and a range consisting of any two of the previous amounts.

In some embodiments, based on about 10 parts by weight of the lamotrigine particles, the pH modifier has an amount selected from the group consisting of one or more of the following: 3.0 parts by weight, 3.1 parts by weight, 3.2 parts by weight, 3.3 parts by weight, 3.4 parts by weight, 3.5 parts by weight, 3.6 parts by weight, 3.7 parts by weight, 3.8 parts by weight, 3.9 parts by weight, 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, the pH modifier is a combination of disodium hydrogen phosphate and critic acid, and based on about 10 parts by weight of the lamotrigine particles, the total amount of the disodium hydrogen phosphate and the critic acid is selected from the group consisting of one or more of the following: 4.0 parts by weight, 4.1 parts by weight, 4.2 parts by weight, 4.3 parts by weight, 4.4 parts by weight, 4.5 parts by weight, 4.6 parts by weight, 4.7 parts by weight, 4.8 parts by weight, 4.9 parts by weight, 5.0 parts by weight, 5.1 parts by weight, 5.2 parts by weight, 5.3 parts by weight, 5.4 parts by weight, 5.5 parts by weight, 5.6 parts by weight, 5.7 parts by weight, 5.8 parts by weight, 5.9 parts by weight, 6.0 parts by weight, 6.1 parts by weight, 6.2 parts by weight, 6.3 parts by weight, 6.4 parts by weight, 6.5 parts by weight, 6.6 parts by weight, 6.7 parts by weight, 6.8 parts by weight, 6.9 parts by weight, 7.0 parts by weight, 7.1 parts by weight, 7.2 parts by weight, 7.3 parts by weight, 7.4 parts by weight, 7.5 parts by weight, 7.6 parts by weight, 7.7 parts by weight, 7.8 parts by weight, 7.9 parts by weight and 8.0 parts by weight, and a range consisting of any two of the previous amounts.

In some embodiments, the pH modifier is critic acid, and based on about 10 parts by weight of the lamotrigine particles, the critic acid has an amount selected from the group consisting of one or more of the following: 0.5 parts by weight, 0.6 parts by weight, 0.7 parts by weight, 0.8 parts by weight, 0.9 parts by weight, 1.0 parts by weight, 1.1 parts by weight, 1.2 parts by weight, 1.3 parts by weight, 1.4 parts by weight, 1.5 parts by weight, 1.6 parts by weight, 1.7 parts by weight, 1.8 parts by weight, 1.9 parts by weight, 2.0 parts by weight, 2.1 parts by weight, 2.2 parts by weight, 2.3 parts by weight, 2.4 parts by weight and 2.5 parts by weight, and a range consisting of any two of the previous amounts.

In some embodiments, the pH modifier is sodium dihydrogen phosphate, and based on about 10 parts by weight of the lamotrigine particles, the sodium dihydrogen phosphate has a mount of 3 parts by weight.

In some embodiments, the lamotrigine hydrate form A in the suspension of the present invention has a particle size selected from the group consisting of the following one or more ranges: 20-80 µm, 20-70 µm, 20-60 µm, 20-50 µm, 20-40 µm, 20-30 µm, 30-80 µm, 30-70 µm, 30-60 µm, 30-50 µm, 30-40 µm, 40-80 µm, 40-70 µm, 40-60 µm, 40-50 µm, 50-80 µm, 50-70 µm, 50-60 µm, 60-80 µm, 60-70 µm and 70-80 µm.

In some embodiments, after standing at 4° C. for 24 hours, standing at the normal temperature for 1 day, standing at the normal temperature for 3 days, standing at the normal temperature for 6 days, standing at the normal temperature for 10 days, standing at the normal temperature for 15 days, and standing at the normal temperature for 1 month, the lamotrigine hydrate form A in the suspension of the present invention has a particle size selected from the group consisting of the following one or more ranges: 20-80 µm, 20-70 µm, 20-60 µm, 20-50 µm, 20-40 µm, 20-30 µm, 30-80 µm, 30-70 µm, 30-60 µm, 30-50 µm, 30-40 µm, 40-80 µm, 40-70 µm, 40-60 µm, 40-50 µm, 50-80 µm, 50-70 µm, 50-60 µm, 60-80 µm, 60-70 µm and 70-80 µm.

Pharmaceutical Cartridge

The lamotrigine and one or more ingredients (for example, a pH modifier, and a preservative) may also be stored separately in different containers (for example, capsules, dispensing vials or boxes) of a pharmaceutical cartridge. The lamotrigine and other ingredients in the pharmaceutical cartridge may be added to water together to prepare the suspension described above. The properties and dosage of the lamotrigine and other ingredients are the same as above.

Therefore, the present invention provides a pharmaceutical cartridge comprising at least one of the compositions previously described herein, at least one of the preparation methods previously described herein to prepare a suspension, at least one of the suspensions previously described herein, or at least one of the dry suspensions previously described herein, where The lamotrigine and other ingredients (for example, selected from the group consisting of one or more of a pH modifier, a preservative, a thickener, a filler, a sweetener, etc.) previously described herein are contained in the same container;

or the lamotrigine and other ingredients (for example, selected from the group consisting of one or more of a pH modifier, a preservative, a thickener, a filler, a sweetener, etc.) previously described herein are contained in one or more different containers.

In some embodiments, lamotrigine particles and other ingredients (for example, selected from the group consisting of one or more of a pH modifier, a preservative, a thickener, a filler, a sweetener, etc.) in the pharmaceutical cartridge are mixed together and then added to water to prepare a suspension.

In some embodiments, the lamotrigine particles in the pharmaceutical cartridge may be mixed with an aqueous solution containing other ingredients (for example, selected from the group consisting of one or more of a pH modifier, a preservative, a thickener, a filler, a sweetener, etc.) to formulate a suspension.

In some embodiment, the suspension, the dry suspension, the lamotrigine and, for example, the pH regulator, the preservative, the thickener, the filler, the sweetener, etc. are defined as described in the preceding sections herein in terms of type, content, D90 particle size, microscopic particle size, anti-microbial stability or the like.

Composition and Product

In another aspect, the present invention provides a composition comprising the lamotrigine hydrate form A of the present invention and one or more pharmaceutically acceptable excipients.

In some embodiments, the composition may further comprise at least one additional medicament. In some embodiments, the composition further comprises one or more additional medicaments selected from the group consisting of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

In some embodiments, the lamotrigine hydrate form A or the composition thereof may also be packaged in a pharmaceutical cartridge together with other medicaments. The lamotrigine hydrate form A or the composition thereof may be administered in combination with other medicaments to a patient simultaneously or successively.

In some embodiments, the composition may administer the lamotrigine hydrate form A described herein to a patient in any suitable dosage form. The dosage form includes, but is not limited to: (a) a dosage form for oral administration, including a capsule, a tablet, a granule, a spray, a syrup and the like; (b) a dosage form for non-oral administration, such as rectal, vaginal, urethral, intraocular, nasal or ear administration, including an aqueous suspension, an oily preparation and the like, or drops, a spray, suppositories, paste, ointments, etc.; (c) a dosage form for administration through for example subcutaneous, intraperitoneal, intravenous, intramuscular, intradermal, intraorbital, intracapsular, intramedullary and intrasternal injection; (d) a dosage form for local administration, including an inhalation solution, a nasal spray, an implant, and the like; and (e) an additional dosage form deemed suitable for delivery of an active ingredient to a target tissue by those skilled in the art.

In some embodiments, the composition is in a dosage form selected from the group consisting of a tablet, a capsule, a powder and a suspension, and preferably a suspension. In some embodiments, the suspension comprising the lamotrigine hydrate form A may be accurately taken (for example, by a doser) and then administered orally.

The exact formula, route of administration and dosage of the composition may be selected by the physician according to the patient's condition. In some embodiments, the lamotrigine hydrate form A is administered to a patient at a dose in a range of about 0.1 mg/kg to 1000 mg/kg. Depending on the patient's need, the dose may be administrated in one or more dose units in one day or over several days. In the case that a determined dose has been used clinically, the composition of the lamotrigine hydrate form A may be used at the determined dose, or in a range of about 0.1% to about 500% of the dose, more preferably of about 25% to about 250% of the dose.

A clinician may know how and when to terminate or adjust the dose based on toxicity or organ dysfunction. Conversely, in case of inadequate clinical reaction (toxic reaction excluded), a clinician may also know how to adjust the therapeutic dose to a higher level. In the disease being treated, the amount of the dose may be adjusted according to the severity of the disease being treated and the route of administration. The severity of the disease may be assessed by, for example, standard prognostic assessment methods. In addition, the dose may also be adjusted according to age, weight and individual differences of patients.

Although the exact dose varies in various situations, in most cases, the dose may be summarized as follows: the daily dosage regimen for an adult patient may be from about 0.1 mg to about 2000 mg, preferably from about 1 mg to about 500 mg and most preferably from about 5 mg to about 200 mg for oral administration; and preferably from about 0.01 mg to about 100 mg and most preferably from about 0.1 mg to about 60 mg for intravenous, subcutaneous or intramuscular injection. In some embodiments, the composition is administered 1-4 times per day. In other cases, the lamotrigine hydrate form A may be administrated by continuous intravenous infusion, preferably at a dose of at most about 1000 mg per day. A skilled person in the art will understand that in some cases, it may be necessary to use the lamotrigine hydrate form A at a dose in excess of or much higher than the above-mentioned preferred dose range, in order to effectively and actively treat a particularly critical condition. In some embodiments, the lamotrigine hydrate form A may be used continuously for one week or several months or several years or more.

In some embodiments, after administration of the composition comprising the lamotrigine hydrate form A, it is released in about 1 hour to 12 hours, preferably 3 hours to 12 hours, more preferably 6 hours to 12 hours. In some embodiments, the orally administered composition of the lamotrigine hydrate form A may be administered 1-4 times per day in a single dose or multiple doses. The oral dosage form may be conveniently administrated in a single dose and may be prepared by methods well known in the pharmaceutical field.

If desired, the composition comprising the lamotrigine hydrate form A may be stored in a packaging material or a dosing device, which may include one or more unit doses.

The packaging material may be a metal or plastic film, or a blister package. The package or dosing device may also be enclosed with instructions. Such instructions may be either prescription medicine labels approved by the Drug Administration, or instructions for formulating the composition comprising the lamotrigine hydrate form A in a compatible container.

In some embodiments, in the composition comprising the lamotrigine hydrate form A, more than about 50%, more than about 60%, more than about 70%, more than about 80%, more than about 90% or more than about 95% of lamotrigine exists in a form of the lamotrigine hydrate form A. In some embodiments, in the composition, more than about 80% of lamotrigine exists in a form of the lamotrigine hydrate form A; preferably, more than about 90% of lamotrigine exists in a form of the lamotrigine hydrate form A; and more preferably, more than about 95% of lamotrigine exists in a form of the lamotrigine hydrate form A.

In some embodiments, the pharmaceutically acceptable excipient is selected from the group consisting of one or more of a thickener, a filler, a sweetener, a pH modifier and a preservative.

In some embodiments, the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations.

In a preferred embodiment, the thickener is selected from the group consisting of one or more of xanthan gum, povidone, colloidal microcrystalline cellulose and sodium alginate, more preferably xanthan gum; and preferably, the content of the thickener is about 1 to 7 parts by weight, preferably about 1 to 5 parts by weight, on the basis that the content of the lamotrigine hydrate form A is about 10 parts by weight.

In a preferred embodiment, the filler is selected from the group consisting of one or more of mannitol, microcrystalline cellulose, sucrose and lactose; and preferably, the content of the filler is about 20 to 60 parts by weight, on the basis that the content of the lamotrigine hydrate form A is about 10 parts by weight.

In a preferred embodiment, the sweetener is selected from the group consisting of one or more of sucralose, aspartame and sodium saccharin; and preferably, the content of the sweetener is about 1-3 parts by weight, on the basis that content of the lamotrigine hydrate form A is about 10 parts by weight.

In a preferred embodiment, the pH modifier is selected from the group consisting of one or more of sodium dihydrogen phosphate, citric acid and sodium citrate; and preferably, the content of the pH modifier is about 2-5 parts by weight, on the basis that the content of the lamotrigine hydrate form A is about 10 parts by weight.

In a preferred embodiment, the preservative is selected from the group consisting of one or more of sodium propylparaben, sodium methylparaben, sodium benzoate and potassium sorbate; and preferably, the content of the preservative is about 1 to 3 parts by weight, on the basis that the content of the lamotrigine hydrate form A is about 10 parts by weight.

In some embodiments, the composition comprises: about 10 parts by weight of the lamotrigine hydrate form A; about 1-5 parts by weight of xanthan gum; about 20-60 parts by weight of mannitol; about 1-3 parts by weight of sucralose; about 2-5 parts by weight of sodium dihydrogen phosphate; and about 1-3 parts by weight of a combination of sodium methylparaben and sodium propylparaben, where the weight ratio of the sodium methylparaben to the sodium propylparaben is about 9:1.

The composition comprising the lamotrigine hydrate form A described above may be prepared from the lamotrigine hydrate form A and other components by a certain formulation method. It may also be prepared from anhydrous lamotrigine, lamotrigine hydrate or lamotrigine salts and other components by a certain formulation method.

In another aspect, the present invention provides a suspension comprising a lamotrigine hydrate form A, a lamotrigine hydrate form A, a solid form comprising the lamotrigine hydrate form A or a composition comprising the lamotrigine hydrate form A, prepared by the method of the present invention. As used herein, the term "solid form" includes all solid forms of lamotrigine, such as crystalline or amorphous forms, or a combination thereof.

In some embodiments, in the suspension comprising the lamotrigine hydrate form A, the lamotrigine hydrate form A, the solid form comprising the lamotrigine hydrate form A or the composition comprising the lamotrigine hydrate form A, more than about 50%, more than about 60%, more than about 70%, more than about 80%, more than about 90% or more than about 95% of lamotrigine exists in a form of the lamotrigine hydrate form A.

Therapeutic Methods and Uses

In another aspect, the present invention provides a method for treating a nervous system disease, comprising administering a therapeutically effective amount of the lamotrigine hydrate form A of the present invention or the composition of the present invention to a subject in need thereof.

In another aspect, the present invention provides a use of the lamotrigine hydrate form A of the present invention or the composition of the present invention in preparation of a medicament for treating a nervous system disease.

In another aspect, the present invention provides the lamotrigine hydrate form A of the present invention or the composition of the present invention for use in treating a nervous system disease.

In some embodiments, the lamotrigine hydrate form A may be used alone, or in combination with other medicaments for treating a nervous system disease.

In some embodiments, the lamotrigine hydrate form A has a purity of more than about 50%, more than about 60%, more than about 70%, more than about 80%, more than about 90%, or more than about 95%. In some embodiments, in the composition comprising the lamotrigine hydrate form A, more than about 50%, more than about 60%, more than about 70%, more than about 80%, more than about 90% or more than about 95% of lamotrigine exists in a form of the lamotrigine hydrate form A; preferably, more than about 90% of lamotrigine exists in a form of the lamotrigine hydrate form A; and more preferably, more than about 95% of lamotrigine exists in a form of the lamotrigine hydrate form A.

In some embodiments, the nervous system disease is selected from the group consisting of one or more of Alzheimer's disease, depression, multiple sclerosis, Parkinson's disease and epilepsy.

In some embodiments, the medicament is used in combination with an additional medicament for treating a nervous system disease, and preferably, the additional medicament is selected from the group consisting of one or more of oxcarbazepine, carbamazepine, topiramate and lacosamide.

In some embodiments, the medicament is in the form of suspension.

In some embodiments, in the medicament, more than about 80% of lamotrigine exists in a form of the lamotrigine were checked at different time points. The results are shown in Table 1:

Unless stated otherwise, the XRPD results in the examples were measured by a Bruker D8 advance x-ray diffraction instrument (Germany), and the microscope results were determined on a Nanpai CM2000S microscope (Nanjing, China).

TABLE 1

| Standing conditions for different formulas | | Appearance | Microscopic particle size | Crystal form by XRPD |
|---|---|---|---|---|
| | | | Check item | |
| Lamotrigine particles of 8 μm | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Lamotrigine particles of 12 μm | Normal temperature at zero point | Milky white suspension | 20-30 μm | Lamotrigine hydrate form A |
| | Normal temperature for 1 week | Milky white suspension | 60-70 μm | Lamotrigine hydrate form A |
| | Normal temperature for 1 month | Milky white suspension | 60-70 μm | Lamotrigine hydrate form A |
| Lamotrigine particles of 60 μm | Normal temperature and zero point | Milky white suspension | 50-70 μm | Lamotrigine hydrate form A containing unknown crystals |
| | Normal temperature for 1 week | Milky white suspension | 50-70 μm | Lamotrigine hydrate form A containing unknown crystals |
| | Normal temperature for 1 month | Milky white suspension | 50-70 μm | Lamotrigine hydrate form A containing unknown crystals | hydrate form A; preferably, more than about 90% of lamotrigine exists in a form of the lamotrigine hydrate form A; and more preferably, more than about 95% of lamotrigine exists in a form of the lamotrigine hydrate form A.

The lamotrigine hydrate form A prepared by the present invention is not only high in purity, but also has good solubility and high chemical stability, as well as a significant improved physical stability in an aqueous phase environment (that is, the suspension prepared by the present invention has a better physical stability). As such, it is suitable for long-term control of epilepsy.

Figure 3:
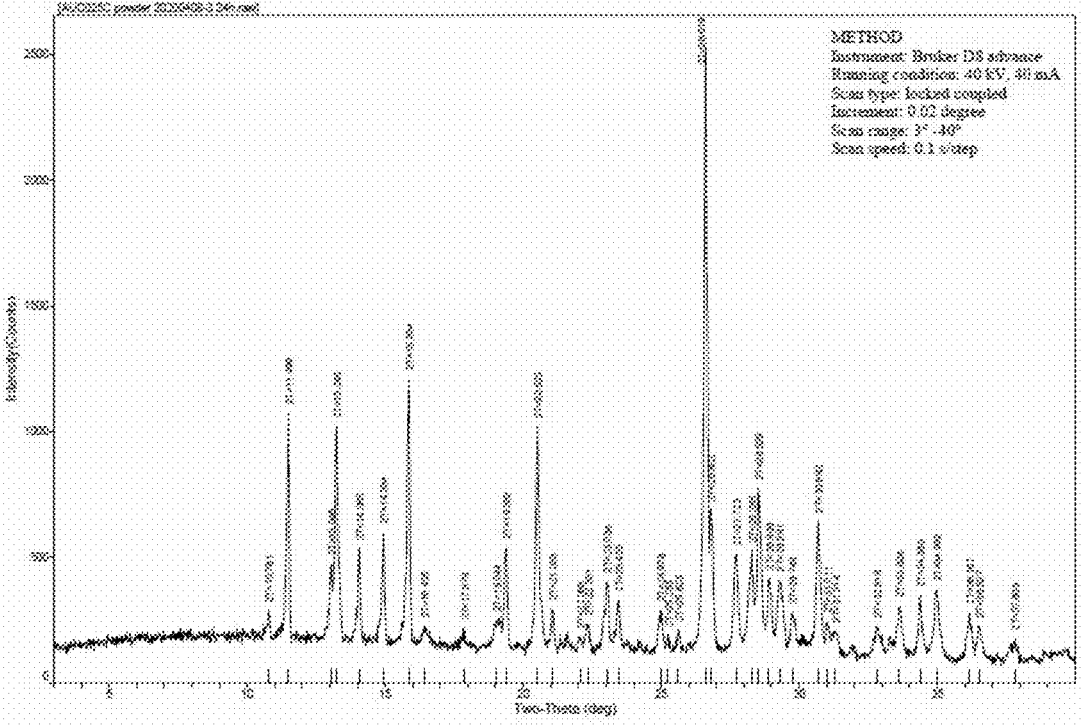
FIG. 3 shows an XRPD pattern of a lamotrigine hydrate form A comprising unknown crystals.

The following examples are only intended to further illustrate the present invention, but the scope of the present invention is not limited to these examples. The raw materials and reagents used herein are commercially available.
Example 1: Preparation of Suspension Comprising Lamotrigine Hydrate Form A Using Lamotrigine Particles Having Different Particle Sizes 10 parts by weight of lamotrigine particles (D90) having a particle size of 8 μm, 12 μm and 60 μm respectively (available from Aurobindo Pharma Co, Ltd, India), and 3 parts by weight of xanthan gum (available from CP Kelco, USA), were added to 1000 parts by weight of purified water. They were dispersed uniformly, and then allowed to stand at 4° C. for 24 hours to obtain a suspension. The resulting suspension was left stood at normal temperature for 1 month, and the suspension and the crystalline forms therein As shown in Table 1, the crystalline form in the suspension is the lamotrigine hydrate form A when using the lamotrigine particles having a particle size of 8 μm and 12 μm, respectively. When using the lamotrigine particles having a particle size of 60 μm, unknown crystals were included in the crystalline form in the suspension, making it impossible to ensure the stability of crystal properties. The XRPD results of the lamotrigine hydrate form A containing unknown crystals are shown in FIG. 3.

Example 2: Preparation of Suspension Comprising Lamotrigine Hydrate Form A Using Different Thickeners 10 parts by weight of lamotrigine particles having a particle size (D90) of 8 μm and 3 parts by weight of a thickener (xanthan gum (available from CP Kelco, USA), povidone (available from BASF, Germany), colloidal microcrystalline cellulose (available from FMC, USA) and sodium alginate (available from Qingdao Bright Moon Seaweed Group Co, Ltd.)) were added to 1000 parts by weight of purified water. They were dispersed uniformly, and then allowed to stand at 4° C. for 24 hours to obtain a suspension. The resulting suspension was left stood at normal temperature for 1 month, and the suspension and the crystalline forms therein were checked at different time points. The results are shown in Table 2:

TABLE 2

| Standing conditions for different formulas | | Appearance | Microscopic particle size | Crystal form by XRPD |
|---|---|---|---|---|
| Xanthan gum as thickener | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Povidone as thickener | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Colloidal microcrystalline cellulose as thickener | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Sodium alginate as thickener | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |

As shown in Table 2, when xanthan gum, povidone, colloidal microcrystalline cellulose and sodium alginate were used as the thickener respectively, the crystalline form in each resulting suspension was the lamotrigine hydrate form A.

Example 3: Preparation of Suspension Comprising Lamotrigine Hydrate Form A Using Different Amounts of Thickeners 10 parts by weight of lamotrigine particles having a particle size (D90) of 8 μm together with xanthan gum of 0 part by weight, 1 part by weight and 5 parts by weight respectively were added to 1000 parts by weight of purified water. They were dispersed uniformly and, then allowed to stand at 4° C. for 24 hours to obtain a suspension. The resulting suspension was left stood at normal temperature for 1 month, and the suspension and the crystalline forms therein were checked at different time points. The results are shown in Table 3:

TABLE 3

| Standing conditions for different formulas | | Appearance | Microscopic particle size | Crystal form by XRPD |
|---|---|---|---|---|
| 0 part by weight of xanthan gum | Normal temperature at zero point | Milky white suspension | 20-30 μm | Lamotrigine hydrate form A |
| | Normal temperature for 1 week | Milky white suspension | 20-30 μm | Lamotrigine hydrate form A containing unknown crystals |
| | Normal temperature for 1 month | Milky white suspension | 20-30 μm | Lamotrigine hydrate form A containing unknown crystals |
| 1 part by weight of xanthan gum | Normal temperature at zero point | Milky white suspension | 20-30 μm | Lamotrigine hydrate form A |
| | Normal temperature for 1 week | Milky white suspension | 20-30 μm | Lamotrigine hydrate form A |

TABLE 3-continued

| Standing conditions for different formulas | | Check item | | |
| --- | --- | --- | --- | --- |
| | | Appearance | Microscopic particle size | Crystal form by XRPD |
| 5 parts by weight of xanthan gum | Normal temperature for 1 month | Milky white suspension | 20-30 μm | Lamotrigine hydrate form A |
| | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |

As shown in Table 3, the crystalline form in the suspension is lamotrigine hydrate form A when using the thickeners of 1 part by weight and 5 parts by weight respectively. Without using the thickener, the crystalline form in the suspension after one week at normal temperature contains unknown crystals, which makes impossible to ensure the stability of crystal properties.

Example 4: Preparation of Suspension Comprising Lamotrigine Hydrate Form A by Standing at Different Low Temperatures 10 parts by weight of lamotrigine particles having a particle size (D90) of 8 μm and 3 parts by weight of xanthan gum were added to 1000 parts by weight of purified water. They were dispersed uniformly, and then allowed to stand at low temperature (−20° C., 4° ° C. and 20° C., respectively) for 24 hours to obtain a suspension. The resulting suspension was left stood at normal temperature for 1 month, and the suspension and the crystalline forms therein were checked at different time points. The results are shown in Table 4:

As shown in Table 4, the crystalline form in the suspension was lamotrigine hydrate form A when standing at a low temperature of −20° C., 4° C. and 20° C., respectively.

Example 5: Preparation of Suspension Comprising Lamotrigine Hydrate Form A by Standing at Low Temperature for Different Periods 10 parts by weight of lamotrigine particles having a particle size (D90) of 8 μm and 3 parts by weight of xanthan gum were added to 1000 parts by weight of purified water. They were dispersed uniformly, and then allowed to stand at 4° C. for 0 hour, 2 hours, 8 hours and 24 hours respectively, to obtain a suspension. The resulting suspension was left stood at normal temperature for 1 month, and the suspension and the crystalline forms therein were checked at different time points. The results are shown in Table 5:

TABLE 4

| Standing conditions for different formulas | | Check item | | |
| --- | --- | --- | --- | --- |
| | | Appearance | Microscopic particle size | Crystal form by XRPD |
| Standing at −20° C. | Normal temperature at zero point | NA | NA | NA |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Standing at 4° C. | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Standing at 20° C. | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |

TABLE 5

| Standing conditions for different formulas | | Appearance | Microscopic particle size | Crystal form by XRPD |
|---|---|---|---|---|
| Standing at 4° C. for 0 hour | Normal temperature at zero point | Milky white suspension | 20-30 μm | Anhydrous |
| | Normal temperature for 1 week | Milky white suspension | 20-30 μm | Lamotrigine hydrate form A containing unknown crystals |
| | Normal temperature for 1 month | Milky white suspension | 20-30 μm | Lamotrigine hydrate form A containing unknown crystals |
| Standing at 4° C. for 2 hours | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Standing at 4° C. for 8 hours | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |
| Standing at 4° C. for 24 hours | Normal temperature at zero point | Milky white suspension | 20-30 μm | Lamotrigine hydrate form A |
| | Normal temperature for 1 week | Milky white suspension | 20-30 μm | Lamotrigine hydrate form A |
| | Normal temperature for 1 month | Milky white suspension | 20-30 μm | Lamotrigine hydrate form A |

As shown in Table 5, the crystalline form in the suspension was lamotrigine hydrate form A when standing at a low temperature for 2 hours, 8 hours and 24 hours, respectively. Without standing at a low temperature (i.e., standing at 4° C. for 0 hour), the crystalline form in the suspension contained unknown crystals after being left stood at normal temperature for one week, which makes it impossible to ensure the stability of crystal properties.

Example 6: Dissolution and Stability 2.5 ml of the resulting suspension prepared by standing at 4° C. for 24 hours described in Example 5 was taken, and the dissolution of the lamotrigine hydrate form A in the suspension was determined by the oar method at a rotating speed of 50 rpm and a temperature of 37±0.5° C., with a dissolution medium of 900 ml of 0.1 N hydrochloric acid. The dissolution exceeded 85% (w/w) within 15 min. This dissolution result was consistent with that of the marketed immediate-release lamotrigine tablets (Lamictal® 25 mg). It shows that the dissolution of the lamotrigine hydrate form A can meet clinical application.

The prepared suspension was left stood at normal temperature for 1 month, and the suspension and crystalline forms therein were checked at different time points, with the following check items: appearance, microscopic particle size, crystalline form by XRPD, dissolution, content and related materials. The results are shown in Table 6. The results obtained at different time points all meet limit requirements, showing that the suspension has good stability and can meet the need for long-term medication of a patient.

Determination of dissolution: The oar method was applied at a rotating speed of 50 rpm and a temperature of 37±0.5° C., with a dissolution medium of 900 ml of 0.1 N hydrochloric acid. Sampling was taken at 15 min, and the dissolution was determined by ultraviolet spectrophotometry.

Determination of content and related materials: A certain amount of suspension was taken, and after reaching a metered volume with a mobile phase and methanol, HPLC was applied for such determination.

TABLE 6

| | | Check item | | | | |
|---|---|---|---|---|---|---|
| Standing condition | Appearance | Microscopic particle size | Crystal form by XRPD | Dissolution content | Content | Related material |
| Limit requirement | Milky white suspension | Not more than 80 μm | hydrate form A | Dissolution exceeding 85% within 15 min | labeled amount 90%-110% of the | Impurity C: not more than 0.2%; unknown individual impurities: not more than 0.2%; total impurities: not more than 1.0% |
| Normal temperature and zero point | Milky white suspension | 20-30 μm | hydrate form A | 95.4% (15 min) | 100.4% | Impurity C: not detected; unknown individual impurities: not detected; total impurities: not detected |
| Normal temperature for 1 month | Milky white suspension | 20-30 μm | hydrate form A | 97.5% (15 min) | 101.1% | Impurity C: not detected; unknown individual impurities: not detected; total impurities: not detected |

Example 7: Preparation of Suspension Comprising Lamotrigine Hydrate Form A Under Different pH Using Lamotrigine Having Initial Particle Size of Less than 8 μm for D90

The suspension was prepared according to the components and their contents (in parts by weight) in each experimental group as shown in Table 7 below, to observe, at different pH values, the appearance of the suspension prepared from lamotrigine particles having different D90 particle sizes and the microscopic particle sizes of the particles in the suspension.

All components of each group shown in Table 7 were placed in a hopper having a suitable size, mixed at 20 rpm for 5 minutes, then screened through 475 μm screen mesh, and subsequently placed in the hopper again and mixed for 10 minutes to obtain a dry suspension available for further applications. The dry suspension is reconstituted into a suspension before administration. The crystalline forms in the suspension were checked at different time points, with the following check items: observation and determination of appearance, microscopic particle size, and crystalline form by XRPD.

TABLE 7

| Group | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| System pH | 4.5 | 4.6 | 4.6 | 5.3 | 5.3 | 5.3 | 5.3 | 5.6 | 4.85 | 5.33 | 5.34 | 5.36 | 5.96 | 6.8 | 6.85 |
| D90 particle size (μm) | 8 | 4.5 | 8 | 4.5 | 8 | 8 | 4.5 | 4.5 | 7.6 | 7.6 | 7.6 | 7.6 | 7.6 | 8 | 7.6 |
| Lamotrigine particles | 10 | 10 | 10 | 10 | 10 | 10 | 10 | 10 | 10 | 10 | 10 | 10 | 10 | 10 | 10 |
| Mannitol | 20 | 20 | 20 | 20 | 20 | 20 | 20 | 20 | 20 | 20 | 20 | 20 | 20 | 20 | 20 |
| Xanthan gum | 3 | 3 | 3 | 3 | 3 | 3 | 3 | 3 | 3 | 3 | 3 | 3 | 3 | 3 | 3 |
| Sucralose | 1 | 1 | 1 | 1 | 1 | 1 | 1 | 1 | 1 | 1 | 1 | 1 | 1 | 1 | 1 |
| Citric Acid | 4.1 | 2.5 | 2.5 | 2.5 | 2.5 | 2.5 | 2.5 | 2.5 | 1.3 | 1 | 0.5 | 1.4 | 1.1 | — | — |
| Disodium hydrogen phosphate | — | — | — | 1.5 | 1.5 | 2 | 2 | 2.6 | — | — | — | — | — | — | — |
| Sodium dihydrogen phosphate | — | — | — | — | — | — | — | — | — | — | — | — | — | 3 | 3 |
| Sodium methylparaben | 2 | 2 | 2 | 2 | 2 | — | 2 | 1.5 | — | — | — | 2 | 2 | 2 | 2 |
| Sodium propylparaben | 0.2 | 0.2 | 0.2 | 0.2 | 0.2 | — | 0.2 | 0.15 | — | — | — | 0.22 | 0.22 | 0.2 | 0.22 |
| Potassium sorbate | — | — | — | — | — | 2 | — | — | — | 2 | 2 | — | — | — | — |
| Sodium benzoate | — | — | — | — | — | — | — | — | 2 | — | — | — | — | — | — |

In the pH range of 4.6-6.85, the suspensions of groups 2-15 showed a milky white appearance after standing at 4° C. for 24 hours. The suspension was measured to contain the lamotrigine hydrate form A, and the particle size was measured in the range of 20-60 μm (Groups 2-6 and Groups 9-10: microscopic particle size of 20-30 μm; Groups 7-8 and Groups 11-12: microscopic particle size of about 30 μm; Groups 13-15: microscopic particle size of 50-60 μm). In this pH range, as an overall trend, the microscopic particle size of the lamotrigine hydrate form A increased with pH value.

After continued standing at normal temperature for 1 day, the suspensions of Groups 2-15 still showed the milky white appearance, and the particle size of the crystals in each group substantially remained unchanged compared with that of the crystals subjected to previous standing at 4° C. for 24 hours. After standing at normal temperature for 6 days, the microscopic particle size of Groups 13-15 increased slightly to 70-80 μm, but the appearance of each suspension was still milky white; and the observation and measurement results of Groups 2-12 were substantially the same as those standing at normal temperature for 1 day, and the particle size of the crystals in the suspensions remained substantially unchanged over this long period of time. Groups 2-15 were observed under a microscope again, and it was found that the lamotrigine hydrate form A sill existed in each suspension. All suspensions from Groups 2-15 showed excellent uniformity and stability after standing at normal temperature for 6 days. In the suspension, more than about 95% of lamotrigine existed in a form of the lamotrigine hydrate form A. Finally, Groups 2-15 also met the anti-microbial effects according to USP<51>.

When the pH was 4.5, the suspension of Group 1 began to show a nonuniform appearance after standing at 4° C. for 24 hours, and obvious bulk crystals were observed by the naked eyes, which seriously affected the uniformity of the suspension. After standing at normal temperature for 6 days, the bulk crystals became more. Oversized crystals would affect the uniformity of the medicament during administration, ultimately leading to inaccurate dosing.

Figure 4A:
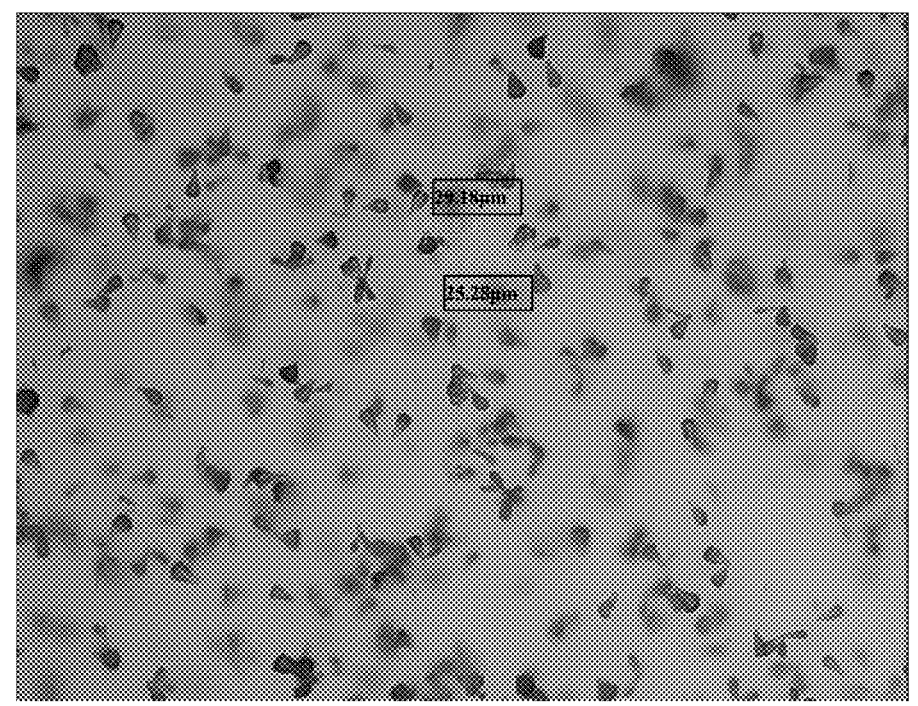
FIG. 4 shows microscopic photographs of lamotrigine hydrate forms A in several representative groups in Table 7.
Figure 4B:
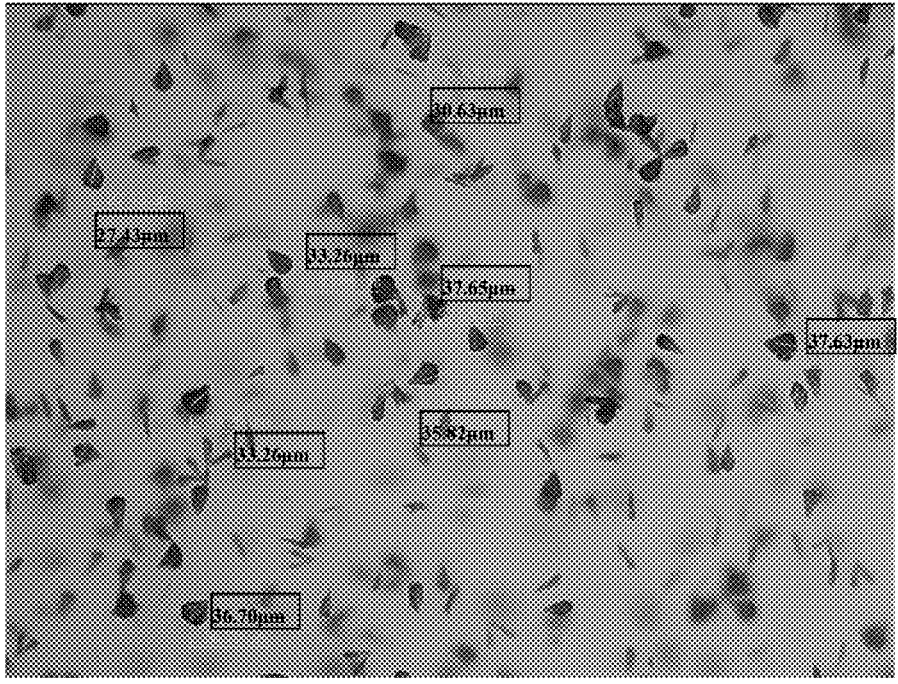
Figure 4C:
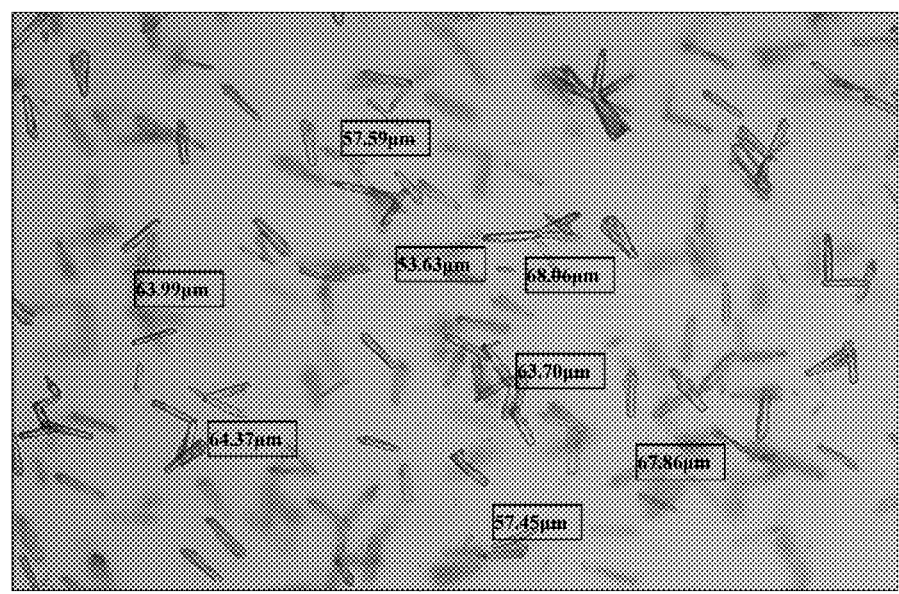

FIG. 4 shows microscopic photographs of lamotrigine hydrate forms A in several representative groups in Table 7. The diagram in FIG. 4A shows a microscopic photograph of a lamotrigine hydrate form A of Group 2 in Table 7, which shows that at pH 4.6, the lamotrigine hydrate form A appears as a melon seed under the microscope. The diagram in FIG. 4B shows a microscope photograph of a lamotrigine hydrate form A of Group 7 in Table 7, which shows that when pH increases to 5.3, the lamotrigine hydrate form A begins to appear as a mixture of short prisms and melon seeds under the microscope. The diagram in FIG. 4C shows a microscopic photograph of a lamotrigine hydrate form A of Group 14 in Table 7, which shows that when pH continues to increase to 6.8, the lamotrigine hydrate form A appears as a short prism under the microscope. The two microscopic particle states of short prisms and melon seeds have no effect on the crystalline form, and they are both A-type crystalline forms that can maintain stable over a certain period of time.

The above results suggest that the pH value has an effect on the stability of the suspension in the form of solution. At the pH of lower than 4.6, it is impossible to form a uniform and stable suspension when the initial particle size for the lamotrigine particle size D90 is 8 μm. In the pH range of 4.6-6.85, when the initial particle size for the lamotrigine particle size D90 is below 8 μm, the suspension can remain uniform and stable over at least one week at normal temperature.

Notably, the pH range of 4.6-5.6 is particularly beneficial to the particle size of the lamotrigine hydrate form A. In this pH range, the lamotrigine hydrate form A not only exhibits an initial microscopic particle size of 20-30 μm, but also remains unchanged after standing at normal temperature over a period of time. In the pH range of greater than 5.6, such as pH 5.9-6.9, the microscopic particle size of the lamotrigine hydrate form A shows a slight increase after a period of time. This suggests that the pH range of 4.6-5.6 is particularly beneficial to the stability in particle size and crystalline form, which is important for the suspension to remain uniform and stable over a long period of time.

Example 8: Preparation of Suspension Comprising Lamotrigine Hydrate Form A Using Different pH and Initial Particle Size of More than 8 μm for D90

The suspension was prepared according to the components and their contents (in parts by weight) in each experimental group as shown in Table 8 below, to observe, at different pH values, the appearance of the suspension prepared from lamotrigine particles having different D90 particle sizes and the microscopic particle sizes of the particles in the suspension.

All components of each group shown in Table 8 were placed in a hopper having a suitable size, mixed at 20 rpm for 5 minutes, then screened through 475 μm screen mesh, and subsequently placed in the hopper again and mixed for 10 minutes to obtain a dry suspension available for further applications. The dry suspension is reconstituted into a suspension before administration. The crystalline forms in the suspension were checked at different time points, with the following check items: observation and determination of appearance, microscopic particle size, and crystalline form by XRPD.

TABLE 8

| Group | 1 | 2 | 3 | 4 | 5 | 6 |
|---|---|---|---|---|---|---|
| System pH | 5.5 | 5.8 | 6.5 | 6.5 | 6.85 | 6.8 |
| D90 particle size (μm) | 12.42 | 12.15 | 12 | 12.42 | 12.42 | 35 |
| Lamotrigine particles | 10 | 10 | 10 | 10 | 10 | 10 |
| Mannitol | 20 | 20 | 20 | 20 | 20 | 20 |
| Xanthan gum | 3 | 3 | 3 | 3 | 3 | 3 |
| Sucralose | 1 | 1 | 1 | 1 | 1 | 1 |
| Citric Acid | 2.5 | 2.5 | 2.5 | 2.5 | — | — |
| Disodium hydrogen phosphate | 2.3 | 3 | 5.5 | 5.5 | — | — |
| Sodium dihydrogen phosphate | — | — | — | — | 3 | 3 |
| Sodium methylparaben | 2 | 2 | 2 | 2 | 2 | 2 |
| Sodium propylparaben | 0.2 | 0.2 | 0.2 | 0.2 | 0.22 | 0.2 |
| Potassium sorbate | | | — | | | — |
| Sodium benzoate | — | — | — | — | — | — |

In the pH range of 5.8-6.85, the suspensions of Groups 2-5 showed a milky white appearance after standing at 4° C. for 24 hours. The suspension was measured to contain the lamotrigine hydrate form A, and the particle size was measured in the range of 20-40 μm (Group 2: microscopic particle size of 30-40 μm; Group 3: microscopic particle size of 20-30 μm; Group 4: microscopic particle size of 20-30 μm; and Group 5: microscopic particle size of 20-30 μm). After standing at normal temperature for 1 day, the suspensions of Groups 2-5 still had a milky white appearance, and it was the lamotrigine hydrate form A still found in the suspensions by means of microscopic observation. After standing at normal temperature for 6 days, the suspension remained unchanged in appearance, and the particle size was substantially the same as that of the suspension after standing at normal temperature for 1 day. In the suspension, more than about 95% of lamotrigine existed in a form of the lamotrigine hydrate form A. This suggests that the pH range of 5.8-6.85 is beneficial to the stability in particle size and crystalline form. In addition, when the particle size D90 of the lamotrigine particles is about 12 μm, the microscope particle size of the lamotrigine hydrate form A decreases with the increase of pH value as an overall trend in the pH range of 5.8-6.85. Finally, Groups 2-5 also met the antimicrobial effects according to USP<51>.

From the above results, it is also found that when the initial particle size of greater than 8 μm is used for D90, bulk crystal agglomeration is observed by the naked eyes after the suspension of Group 1 (pH of less than 5.8) is stood at 4° C. for 24 hours, and the agglomeration can no longer be dispersed, which seriously affects the uniformity of the suspension. After standing at normal temperature for 6 days, the bulk crystals became more.

From the above results, it is also found that when the excessive initial particle size is used for D90 (for example, the initial particle size of 35 μm is used for D90 in Group 6), the suspension can be observed with a nonuniform appearance by the naked eye after standing at 4° C. for 24 hours in the pH range of 6.8.

The above results suggest that the pH value has an effect on the stability of the suspension in the form of solution, and the range of pH value applicable to different initial particle sizes for D90 is different. When the initial particle size for the lamotrigine particle size D90 is about 12 μm, the pH value for maintaining the suspension uniform and stable is above 5.8. In the pH range of 5.8-6.85, when the initial particle size for the lamotrigine particle size D90 is about 12 μm, the suspension can remain uniform and stable over at least one week at normal temperature.

It can be expected that the pH value of the suspension will also affect the uniformity and stability of the suspension with the initial particle size for the lamotrigine particle size D90 ranging from 8 μm to 12 μm.

Example 9

10 parts by weight of lamotrigine particles having a particle size (D90) of 12 μm and 7 parts by weight of xanthan gum were added to 1000 parts by weight of purified water. They were dispersed uniformly, and then allowed to stand at 4° C. for 24 hours to obtain a suspension comprising a lamotrigine hydrate form A. The suspension was filtered to obtain the lamotrigine hydrate form A.

The obtained lamotrigine hydrate form A was analyzed by XRPD. The XRPD pattern of the lamotrigine hydrate form A has a series of characteristic peaks at diffraction angles (2θ) of 11.5±0.2, 13.4±0.2, 15.0±0.2, 16.5±0.2, 19.2±0.2, 26.9±0.2 and 27.7±0.2 degrees, and no characteristic peak at a diffraction angle (2θ) of 15.9±0.2 degrees.

The obtained lamotrigine hydrate form A was quantitatively analyzed by XRPD. $Al_2O_3$ was selected as the standard material, and the XRPD was performed using a Bruker D8 advance instrument under a voltage of 40 kV, a current of 40 mA, a step of 0.02 degrees, and a scanning speed of 0.1 second/step. The purity of the lamotrigine hydrate form A was measured as 87.2% (w/w).

Example 10

10 parts by weight of lamotrigine particles having a particle size (D90) of 8 μm and 3 parts by weight of povidone were added to 1000 parts by weight of purified water. They were dispersed uniformly, and then allowed to stand at 20° C. for 2 hours to obtain a suspension comprising a lamotrigine hydrate form A. The suspension was filtered to obtain the lamotrigine hydrate form A.

The obtained lamotrigine hydrate form A was analyzed by XRPD. The XRPD pattern of the lamotrigine hydrate form A has a series of characteristic peaks at diffraction angles (2θ) of 11.5±0.2, 13.4±0.2, 15.0±0.2, 16.5±0.2, 19.2±0.2, 26.9±0.2 and 27.7±0.2 degrees, and no characteristic peak at diffraction angles (2θ) of 23.5±0.2, 28.2±0.2 and 30.7±0.2 degrees.

The lamotrigine hydrate form A showed an appearance of short prism under a microscope.

The obtained lamotrigine hydrate form A was quantitatively analyzed by XRPD. $Al_2O_3$ was selected as the standard material, and the XRPD was performed using a Bruker D8 advance instrument under a voltage of 40 kV, a current of 40 mA, a step of 0.02 degrees, and a scanning speed of 0.1 second/step. The purity of the lamotrigine hydrate form A was measured as 91.4% (w/w).

Example 11

10 parts by weight of lamotrigine particles having a particle size (D90) of 8 μm and 3 parts by weight of xanthan gum were added to 1000 parts by weight of purified water. They were dispersed uniformly, and then allowed to stand at 4° C. for 24 hours to obtain a suspension comprising a lamotrigine hydrate form A. The suspension was filtered to obtain the lamotrigine hydrate form A.

The obtained lamotrigine hydrate form A was analyzed by XRPD. The XRPD pattern of the lamotrigine hydrate form A has a series of characteristic peaks at diffraction angles (2θ) of 11.5±0.2, 13.4±0.2, 15.0±0.2, 16.5±0.2, 19.2±0.2, 26.9±0.2 and 27.7±0.2 degrees, and no characteristic peak at diffraction angles (2θ) of 15.9±0.2, 20.5±0.2, 23.5±0.2, 28.2±0.2 and 30.7±0.2 degrees.

The obtained lamotrigine hydrate form A was quantitatively analyzed by XRPD. $Al_2O_3$ was selected as the standard material, and the XRPD was performed using a Bruker D8 advance instrument under a voltage of 40 kV, a current of 40 mA, a step of 0.02 degrees, and a scanning speed of 0.1 second/step. The purity of the lamotrigine hydrate form A was measured as 97.7% (w/w). It has an XRPD pattern shown in FIG. 1. Its appearance under a microscope is shown in FIG. 2.

Example 12 Suspension 10 parts by weight of lamotrigine particles having a particle size (D90) of 8 μm, 5 parts by weight of xanthan gum, 20 parts by weight of mannitol (available from Roquette, France), 1 part by weight of sucralose (available from Merck, Germany) and 2 parts by weight of sodium dihydrogen phosphate (available from Spectrum Chemical Mfg. Corp, USA) and 1 part by weight of sodium methylparaben (available from Spectrum Chemical Mfg. Corp, USA) were added to 5000 parts by weight of purified water. They were dispersed uniformly, and then allowed to stand at 20° C. for 30 minutes, to obtain a suspension comprising a lamotrigine hydrate form A. The resulting suspension is a suspension comprising the lamotrigine hydrate form A that is ready for use in a patient.

Example 13 Dry Suspension 10 parts by weight of lamotrigine particles having a particle size (D90) of 30 μm, 3 parts by weight of xanthan gum, 20 parts by weight of mannitol, 1 part by weight of sucralose, 2 parts by weight of sodium dihydrogen phosphate and 2 parts by weight of a combination of sodium methylparaben and sodium propylparaben (with a weight ratio of the sodium methylparaben to the sodium propylparaben being 9:1) were screened through a 1016 micron screen mesh respectively, and then were all placed in a hopper having a suitable size and mixed at 20 rpm for 10 minutes. A dry suspension was obtained for further application.

The above-mentioned dry suspension was added to purified water for reconstitution before administration to a patient. The dry suspension was added to purified water, and the mixture was uniformly dispersed by shaking manually, then allowed to stand at 4° C. for 24 hours to obtain the suspension containing the lamotrigine hydrate form A ready for use in a patient.

Example 14

All components of the formula shown in Table 7 were screened through a 1016 um screen mesh respectively, and then were all placed in a hopper having a suitable size and mixed at 20 rpm for 10 minutes. A dry suspension was obtained for further application. The above-mentioned dry suspension was added to purified water for reconstitution before administration to a patient. The dry suspension was added to purified water, and the mixture was uniformly dispersed by shaking manually, then allowed to stand at 4° C. for 24 hours to obtain the suspension containing the lamotrigine hydrate form A ready for use in a patient.

In the suspension, more than about 95% of lamotrigine existed in a form of the lamotrigine hydrate form A.

TABLE 7

| Ingredient | Dosage, g/bottle | Function |
| --- | --- | --- |
| Lamotrigine particles (D90 = 8 μm) | 1 | Active ingredient |
| Sucrose | 2 | Filler |
| Xanthan gum | 0.3 | Thickener |
| Sodium dihydrogen phosphate | 0.3 | pH modifier |
| Sucralose | 0.1 | Sweetener |
| Sodium methylparaben | 0.18 | Preservative |
| Sodium propylparaben | 0.02 | Preservative |

Embodiment 15: Tablet 10 parts by weight of lamotrigine hydrate form A and 30 parts by weight of microcrystalline cellulose were screened through a 1016 um screen mesh respectively, and then were all placed in a hopper having a suitable size and mixed at 20 rpm for 10 minutes. The mixture was placed in a tablet press to be pressed at 20 rpm and a hardness of 80N, resulting in a tablet containing the lamotrigine hydrate form A ready for use in a patient. The specification of the tablet is 100 mg. The tablet may be used for treating a nervous system disease.

Embodiment 16: Capsule 10 parts by weight of lamotrigine hydrate form A, 10 parts by weight of oxcarbazepine, 3 parts by weight of xanthan gum and 30 parts by weight of lactose were screened through a 1016 um screen mesh respectively. They were then all placed in a hopper having a suitable size and mixed at 20 rpm for 10 minutes. The mixture was placed in a wet granulator, and water was added to prepare wet particles at a shearing speed of 200 rpm and a stirring speed of 200 rpm. After the granulating, the wet particles were dried over a fluidized bed at 40° C. to obtain dry particles, which were then screened through a 1016 um screen mesh to obtain particles of a formulation. After filling the particles into 1 #capsules by a capsule filling machine, capsules containing the lamotrigine hydrate form A ready for use in a patient were obtained. The capsules can be used for treating epilepsy.

The above-mentioned examples are only intended to describe several embodiments of the present invention, which were described specifically in details, but should not be understood as limitation to the scope of the present invention. It should be noted that, for those skilled in the art, several variations and modifications may also be made without departing from the concept of the present invention. Such variations and modifications shall fall within the protection scope of the present invention. Therefore, the protection scope of the present invention is subject to the appended claims Technical Solution Set Technical Solution Group A:

1. A pharmaceutical composition, comprising a therapeutically effective amount of lamotrigine particles and one or more pharmaceutically acceptable excipients, wherein the lamotrigine particles have a particle size (D90) of about 1-30 μm, and the excipients comprise a thickener and a pH modifier; and the pH modifier has an amount such that the pharmaceutical composition is mixed with an aqueous phase to subsequently obtain a suspension having a pH of 4.6-6.9.

2. The pharmaceutical composition according to technical solution 1, the pharmaceutical composition is a dry suspension.

3. The pharmaceutical composition according to anyone of technical solutions 1-2, wherein the pH modifier is selected from the group consisting of one or a combination of more of sodium dihydrogen phosphate, disodium hydrogen phosphate, citric acid, and sodium citrate; and/or wherein based on about 10 parts by weight of the lamotrigine particles, the pH modifier is about 0.5-8 parts by weight.

4. The pharmaceutical composition according to anyone of technical solutions 1-3, wherein after the pharmaceutical composition is mixed with the aqueous phase to form the suspension, more than about 80%, 85%, 90% or 95% of lamotrigine exists in a form of the lamotrigine hydrate form A; and/or after said pharmaceutical composition is mixed with said aqueous phase to form said suspension, said lamotrigine hydrate form A in said suspension has a particle size of 20-80 μm.

5. The pharmaceutical composition according to technical solution 4, wherein an XRPD pattern of the lamotrigine hydrate form A comprises characteristic peaks at diffraction angles $2\theta$ of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles $2\theta$ of about 15.9±0.2, 20.5±0.2, 23.5±0.2, 28.2±0.2, and 30.7±0.2 degrees; and/or, said XRPD pattern of said lamotrigine hydrate form A has no characteristic peaks at diffraction angles $2\theta$ of about 15.9±0.2, 20.5±0.2, 23.5±0.2, 28.2±0.2 and 30.7±0.2 degrees; or wherein said XRPD pattern of said lamotrigine hydrate form A comprises characteristic peaks at diffraction angles $2\theta$ substantially the same as diffraction angles $2\theta$ shown in FIG. 1; or wherein said XRPD pattern of said lamotrigine hydrate form A has XRPD peak positions substantially the same as XRPD peak positions shown in FIG. 1; or wherein said XRPD pattern of said lamotrigine hydrate form A has XRPD peak positions the same as XRPD peak positions shown in FIG. 1.

6. The pharmaceutical composition according to anyone of technical solutions 1-5, wherein the lamotrigine particles have a particle size (D90) of about 4.5-8 μm, and the pH modifier has an amount such that the suspension has a pH of about 4.6-6.9; and/or, based on about 10 parts by weight of the lamotrigine particles, the pH modifier is about 0.5-5.1 parts by weight; and/or, the pH modifier is selected from the group consisting of one or a combination of more of sodium dihydrogen phosphate, disodium hydrogen phosphate, citric acid, and sodium citrate.

7. The pharmaceutical composition according to anyone of technical solutions 1-5, wherein the lamotrigine particles have a particle size (D90) of about 12-13 μm, and the pH modifier has an amount such that the suspension has a pH of about 5.8-6.9; and/or, based on about 10 parts by weight of the lamotrigine particles, the pH modifier is about 3-8 parts by weight; and/or, the pH modifier is selected from the group consisting of one or a combination of more of sodium dihydrogen phosphate, disodium hydrogen phosphate, citric acid, and sodium citrate.

8. The pharmaceutical composition according to anyone of technical solutions 1-7, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

optionally, said thickener is selected from the group consisting of xanthan gum, povidone, colloidal microcrystalline cellulose, sodium alginate and their combinations;

optionally, said thickener is xanthan gum; and/or based on about 10 parts by weight of said lamotrigine particles, said thickener is about 1-7 parts by weight.

9. The pharmaceutical composition according to anyone of technical solutions 1-8, further comprising a preservative, optionally, wherein said preservative is one or a combination of more of sodium propylparaben, sodium methylparaben, sodium benzoate, and potassium sorbate; and optionally, wherein based on about 10 parts by weight of said lamotrigine particles, said preservative is about 1-3 parts by weight.

10. The pharmaceutical composition according to anyone of technical solutions 1-9, further comprising a filler, optionally, wherein the filler is one or a combination of more of mannitol, microcrystalline cellulose, sucrose, and lactose; and optionally, wherein based on about 10 parts by weight of the lamotrigine particles, the preservative is about 20-60 parts by weight.

11. The pharmaceutical composition according to anyone of technical solutions 1-10, further comprising a sweetener, optionally, wherein the sweetener is one or a combination of more of sucralose, aspartame, and sodium saccharin; and optionally, wherein based on about 10 parts by weight of the lamotrigine particles, the sweetener is about 1-3 parts by weight.

12. The pharmaceutical composition according to anyone of technical solutions 1-11, further comprising a preservative, a sweetener, and a filler, optionally, wherein said preservative is one or a combination of more of sodium propylparaben, sodium methylparaben, sodium benzoate, and potassium sorbate; and/or wherein based on about 10 parts by weight of said lamotrigine particles, said preservative is about 1-3 parts by weight;

optionally, wherein said filler is one or a combination of more of mannitol, microcrystalline cellulose, sucrose, and lactose; and/or wherein based on about 10 parts by weight of said lamotrigine particles, said filler is about 20-60 parts by weight; and optionally, wherein said sweetener is one or a combination of more of sucralose, aspartame, and sodium saccharin; and/or based on about 10 parts by weight of said lamotrigine particles, said sweetener is about 1-3 parts by weight.

13. The pharmaceutical composition according to anyone of technical solutions 1-12, wherein the lamotrigine particles have a particle size (D90) of 4.5 μm or 8 μm, and the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

14. The pharmaceutical composition according to anyone of technical solutions 1-13, which can further comprise an additional medicament for a nervous system disease, wherein, optionally, the additional medicament is one or more selected from the group consisting of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

15. The pharmaceutical composition according to anyone of technical solutions 1-13, wherein an appropriate particle size (D90) of the lamotrigine particles is selected to provide a range such that the lamotrigine hydrate form A in the suspension has the following increases in particle size: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

16. A suspension prepared from the pharmaceutical composition according to anyone of technical solutions 1-15 by mixing the pharmaceutical composition according to anyone of technical solutions 1-14 with an aqueous phase.

Technical Solution Group B:

1. A pharmaceutical composition comprising a therapeutically effective amount of lamotrigine particles and one or more pharmaceutically acceptable excipients, wherein a particle size (D90) of the lamotrigine particles is selected such that the lamotrigine particles are reconstituted in an aqueous phase to provide a lamotrigine hydrate form A having a particle size selected from the group consisting of the following one or more ranges: 20-80 µm, 20-70 µm, 20-60 µm, 20-50 µm, 20-40 µm, 20-30 µm, 30-80 µm, 30-70 µm, 30-60 µm, 30-50 µm, 30-40 µm, 40-80 µm, 40-70 µm, 40-60 µm, 40-50 µm, 50-80 µm, 50-70 µm, 50-60 µm, 60-80 µm, 60-70 µm and 70-80 µm;

and wherein an XRPD pattern of the lamotrigine hydrate form A comprises characteristic peaks at diffraction angles (2θ) of about 11.5±0.2, 13.4±0.2, 15.0±0.2, 16.5±0.2, 19.2±0.2, 26.9±0.2, and 27.7±0.2 degrees, and has no characteristic peak(s) at one or more of diffraction angles (2θ) of about 15.9±0.2, 20.5±0.2, 23.5±0.2, 28.2±0.2, and 30.7±0.2 degrees, or, the XRPD pattern of the lamotrigine hydrate form A has no characteristic peak at diffraction angles (2θ) of about 15.9±0.2, 20.5±0.2, 23.5±0.2, 28.2±0.2 and 30.7±0.2 degrees; or the XRPD pattern of the lamotrigine hydrate form A comprises characteristic peaks at diffraction angles (2θ) substantially the same as diffraction angles shown in FIG. 1; or the XRPD pattern of the lamotrigine hydrate form A is substantially the same as that shown in FIG. 1.

2. The pharmaceutical composition according to technical solution 1, wherein the particle size (D90) of the lamotrigine particles is selected from the group consisting of one or more of the following: 4.5 µm, 4.6 µm, 4.7 µm, 4.8 µm, 4.9 µm, 5.3 µm, 5.1 µm, 5.2 µm, 5.3 µm, 5.4 µm, 5.5 µm, 5.6 µm, 5.7 µm, 5.8 µm, 5.9 µm, 6.0 µm, 6.1 µm, 6.2 µm, 6.3 µm, 6.4 µm, 6.5 µm, 6.6 µm, 6.7 µm, 6.8 µm, 6.9 µm, 7.0 µm, 7.1 µm, 7.2 µm, 7.3 µm, 7.4 µm, 7.5 µm, 7.6 µm, 7.7 µm, 7.8 µm, 7.9 µm and 8.0 µm, and a particle size (D90) range consisting of any two of the preceding particles sizes (D90), for example, 6-14 µm, 8-12 µm, 8-10 µm, 7-9 µm, 8-9 µm, 10-12 µm, 11-12 µm or 11-13 µm.

3. The pharmaceutical composition according to technical solution 1 or 2, further comprising a pH modifier, wherein an appropriate pH modifier (in terms of type and/or content) is selected to control such that a suspension obtained by reconstituting the lamotrigine particles in an aqueous phase has a pH selected from the group consisting of one or more of the following pH: 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the previous pH, for example, 4.0-7.0, 4.2-6.8, 4.4-6.8, 4.6-6.8, 4.6-6.6, 4.6-6.4, 4.6-6.2, 4.6-6.0, 4.6-5.8, 4.6-5.6, 4.6-5.4, 4.8-5.2, 5.0-6.8, 5.2-6.8, 5.4-6.8, 5.6-6.8, 5.8-6.8, 6.0-6.8, 6.0-6.6, 6.8-6.6, 5.8-6.6, 5.8-6.4, or 6.0-6.4;

optionally, an appropriate pH modifier (in terms of type and/or content) is selected to control such that a suspension obtained by reconstituting the lamotrigine particles in an aqueous phase has a particle size selected from the group consisting of one or more of the following ranges: 20-80 µm, 20-70 µm, 20-60 µm, 20-50 µm, 20-40 µm, 20-30 µm, 30-80 µm, 30-70 µm, 30-60 µm, 30-50 µm, 30-40 µm, 40-80 µm, 40-70 µm, 40-60 µm, 40-50 µm, 50-80 µm, 50-70 µm, 50-60 µm, 60-80 µm, 60-70 µm and 70-80 µm;

optionally, an appropriate pH modifier (in terms of type and/or content) is selected to control such that a suspension obtained by reconstituting the lamotrigine particles in an aqueous phase has stability defined by A-4.

4. The pharmaceutical composition according to anyone of technical solutions 1-3, wherein an appropriate pH modifier (in terms of type and/or content) is selected to provide a pH range such that the lamotrigine hydrate form A has the following increases in particle size: the particle size increased by less than 30%, less than 20%, less than 10% or less than 5% in the range of about Day 1, about Day 2, about Day 3, about Day 5, about Week 1, about Week 2, about Week 3, about Week 4, about Week 6 or about Week 8.

5. The pharmaceutical composition according to anyone of technical solutions 1-4, wherein an appropriate particle size (D90) of the lamotrigine particles is selected to provide a range such that the lamotrigine hydrate form A in the suspension has the following increases in particle size: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

6. The pharmaceutical composition according to anyone of technical solutions 1-5, further comprising a preservative, wherein the preservative provides an anti-microbial stability lasting for at least one week, at least two weeks, at least three weeks, at least one month, at least two months or at least three months, following the acceptance criteria provided in the USP<51>; and optionally, the acceptance criteria provided in the USP<51> are as follows:

Bacteria: on day 14, the log value of bacterial count decreased by not less than 1.0 as compared with the initial time point, and from Day 14 to Day 28, the log value of bacterial count does not increase; and Yeast and Mold: on Day 14 and Day 28, there is no increase with respect to the initial count.

Technical Solution Group C:

1. A pharmaceutical composition, comprising a therapeutically effective amount of lamotrigine particles and one or more pharmaceutically acceptable excipients, wherein the pharmaceutical composition is reconstituted in an aqueous phase to subsequently form a suspension comprising a lamotrigine hydrate form A, and the lamotrigine particles have a particle size (D90) such that the lamotrigine hydrate form A in the suspension has a particle size selected from the group consisting of at least one of the following: 20-80 µm, 20-70 µm, 20-60 µm, 20-50 µm, 20-40 µm, 20-30 µm, 30-80 µm, 30-70 µm, 30-60 µm, 30-50 µm, 30-40 µm, 40-80 µm, 40-70 µm, 40-60 µm, 40-50 µm, 50-80 µm, 50-70 µm, 50-60 µm, 60-80 µm, 60-70 µm and 70-80 µm; and the excipients comprise a thickener and a pH modifier, and the pH modifier has an amount such that the pharmaceutical composition and an aqueous phase are mixed to subsequently obtain a suspension having a pH of about 4.6-6.9.

2. The pharmaceutical composition according to technical solution 1, wherein the pH modifier is selected from the group consisting of one or a combination of more of sodium dihydrogen phosphate, disodium hydrogen phosphate, citric acid, and sodium citrate; and/or wherein based on 10 parts by weight of the lamotrigine particles, the pH modifier is 0.5-8 parts by weight.

3. The pharmaceutical composition according to anyone of technical solutions 1-2, wherein after the pharmaceutical composition is mixed with the aqueous phase to form the suspension, more than about 80%, 85%, 90% or 95% of lamotrigine exists in a form of the lamotrigine hydrate form A.

4. The pharmaceutical composition according to anyone of technical solutions 1-3, wherein an XRPD pattern of the lamotrigine hydrate form A comprises characteristic peaks at diffraction angles (2θ) of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles 2θ of about 15.9±0.2, 20.5±0.2, 23.5±0.2, 28.2±0.2, and 30.7±0.2 degrees; and/or, said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or wherein said XRPD pattern of said lamotrigine hydrate form A comprises characteristic peaks at diffraction angles 2θ substantially the same as diffraction angles shown in FIG. 1; or wherein said XRPD pattern of said lamotrigine hydrate form A has XRPD peak positions substantially the same as XRPD peak positions shown in FIG. 1; or wherein said XRPD pattern of said lamotrigine hydrate form A has XRPD peak positions the same as XRPD peak positions shown in FIG. 1.

5. The pharmaceutical composition according to anyone of technical solutions 1-4, wherein the lamotrigine particles have a particle size (D90) such that the lamotrigine hydrate form A in the suspension has a particle size of 20-60 μm, and the pH modifier has an amount such that the pharmaceutical composition is mixed with the aqueous phase to obtain a suspension having a pH of 4.6-6.9; and optionally, the lamotrigine particles have a particle size (D90) of 4.5-8 μm.

6. The pharmaceutical composition according to technical solution 5, wherein based on 10 parts by weight of the lamotrigine particles, the pH modifier is 0.5-5.1 parts by weight; and/or, the pH modifier is selected from the group consisting of one or a combination of more of sodium dihydrogen phosphate, disodium hydrogen phosphate, citric acid, and sodium citrate.

7. The pharmaceutical composition according to anyone of technical solutions 1-4, wherein the lamotrigine particles have a particle size (D90) such that the lamotrigine hydrate form A in the suspension has a particle size of 20-40 μm, and the pH modifier has an amount such that the pharmaceutical composition is mixed with the aqueous phase to obtain a suspension having a pH of 5.8-6.9; and optionally, the lamotrigine particles have a particle size (D90) of 12-13 μm.

8. The pharmaceutical composition according to technical solution 7, wherein based on 10 parts by weight of the lamotrigine particles, the pH modifier is 3-8 parts by weight; and/or, the pH modifier is selected from the group consisting of one or a combination of more of sodium dihydrogen phosphate, disodium hydrogen phosphate, citric acid, and sodium citrate.

9. The pharmaceutical composition according to anyone of technical solutions 1-8, wherein the lamotrigine hydrate form A has a particle size achieved by standing the suspension at 4° C. for 24 hours.

10. The pharmaceutical composition according to anyone of technical solutions 1-9, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

optionally, said thickener is selected from the group consisting of xanthan gum, povidone, colloidal microcrystalline cellulose, sodium alginate and their combinations;

optionally, said thickener is xanthan gum; and/or based on 10 parts by weight of the lamotrigine particles, the thickener is 1-7 parts by weight.

11. The pharmaceutical composition according to anyone of technical solutions 1-10, further comprising a preservative, optionally, wherein said preservative is one or a combination of more of sodium propylparaben, sodium methylparaben, sodium benzoate, and potassium sorbate; and optionally, wherein based on 10 parts by weight of the lamotrigine particles, the preservative is 1-3 parts by weight.

12. The pharmaceutical composition according to anyone of technical solutions 1-11, further comprising a filler, optionally, wherein the filler is one or a combination of more of mannitol, microcrystalline cellulose, sucrose, and lactose; and optionally, wherein based on 10 parts by weight of the lamotrigine particles, the filler is 20-60 parts by weight.

13. The pharmaceutical composition according to anyone of technical solutions 1-12, further comprising a sweetener, optionally, wherein the sweetener is one or a combination of more of sucralose, aspartame, and sodium saccharin; and optionally, wherein based on 10 parts by weight of the lamotrigine particles, the sweetener is 1-3 parts by weight.

14. The pharmaceutical composition according to anyone of technical solutions 1-13, further comprising a preservative, a sweetener, and a filler, optionally, wherein the preservative is one or a combination of more of sodium propylparaben, sodium methylparaben, sodium benzoate, and potassium sorbate; and/or wherein based on 10 parts by weight of the lamotrigine particles, the preservative is about 1-3 parts by weight;

optionally, wherein the filler is one or a combination of more of mannitol, microcrystalline cellulose, sucrose, and lactose; and/or wherein based on 10 parts by weight of the lamotrigine particles, the filler is about 20-60 parts by weight;

optionally, wherein the sweetener is one or a combination of more of sucralose, aspartame, and sodium saccharin; and/or wherein based on 10 parts by weight of the lamotrigine particles, the sweetener is about 1-3 parts by weight.

15. The pharmaceutical composition according to anyone of technical solutions 1-14, wherein the lamotrigine particles have a particle size (D90) of 4.5 μm or 8 μm, the lamotrigine hydrate form A in the suspension has a particle size of 20-30 μm, the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

16. The pharmaceutical composition according to anyone of technical solutions 1-15, which can further comprise an additional medicament for a nervous system disease, wherein, optionally, the additional medicament is one or more selected from the group consisting of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

Technical Solution Group D:

1. A suspension comprising a lamotrigine hydrate form A, wherein the suspension comprises the lamotrigine hydrate form A, a thickener, and a pH modifier, and wherein the lamotrigine hydrate form A in the suspension has a particle size being at least one selected from the group consisting of: 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm, and 70-80 μm, and the pH modifier provides a pH of 4.6-6.9 for the suspension.

2. The suspension according to technical solution 1, wherein the pH modifier is selected from the group consisting of one or a combination of more of sodium dihydrogen phosphate, disodium hydrogen phosphate, citric acid, and sodium citrate; and/or
   wherein based on 10 parts by weight of the lamotrigine particles, the pH modifier is 0.5-8 parts by weight.

3. The suspension according to anyone of technical solutions 1-2, wherein an XRPD pattern of the lamotrigine hydrate form A comprises characteristic peaks at diffraction angles (2θ) of about 11.5±0.2, 13.4=0.2, 15.3=0.2, 16.5=0.2, 19.2±0.2, 26.9±0.2, and 27.7±0.2 degrees, and has no characteristic peak(s) at one or more of diffraction angles 2θ of about 15.9±0.2, 20.5=0.2, 23.5±0.2, 28.2±0.2, and 30.7±0.2 degrees; and/or
   said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or
   wherein said XRPD pattern of said lamotrigine hydrate form A comprises characteristic peaks at diffraction angles 2θ substantially the same as diffraction angles shown in FIG. 1; or
   wherein said XRPD pattern of said lamotrigine hydrate form A has XRPD peak positions substantially the same as XRPD peak positions shown in FIG. 1; or
   wherein said XRPD pattern of said lamotrigine hydrate form A has XRPD peak positions the same as XRPD peak positions shown in FIG. 1.

4. The suspension according to anyone of technical solutions 1-3, wherein the lamotrigine hydrate form A is formed by lamotrigine particles having a particle size (D90) of 4.5-8 μm, and the pH modifier has an amount such that the suspension has a pH of about 4.6-6.9; and/or,
   based on 10 parts by weight of the lamotrigine particles, the pH modifier is 0.5-5.1 parts by weight; and/or,
   said pH modifier is selected from the group consisting of one or a combination of more of sodium dihydrogen phosphate, disodium hydrogen phosphate, citric acid, and sodium citrate.

5. The suspension according to anyone of technical solutions 1-3, wherein the lamotrigine hydrate form A is formed by lamotrigine particles having a particle size (D90) of 12-13 μm, and the pH modifier has an amount such that the suspension has a pH of about 5.8-6.9; and/or,
   based on 10 parts by weight of the lamotrigine particles, the pH modifier is 3-8 parts by weight; and/or,
   said pH modifier is selected from the group consisting of one or a combination of more of sodium dihydrogen phosphate, disodium hydrogen phosphate, citric acid, and sodium citrate.

6. The suspension according to anyone of technical solutions 1-5, wherein more than about 80%, 85%, 90% or 95% of lamotrigine in the suspension exists in a form of the lamotrigine hydrate form A.

7. The suspension according to anyone of technical solutions 1-6, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;
   optionally, said thickener is selected from the group consisting of xanthan gum, povidone, colloidal microcrystalline cellulose, sodium alginate and their combinations;
   optionally, said thickener is xanthan gum; and/or
   based on 10 parts by weight of the lamotrigine particles, the thickener is 1-7 parts by weight.

8. The suspension according to anyone of technical solutions 1-7, further comprising a preservative,
   optionally, wherein said preservative is one or a combination of more of sodium propylparaben, sodium methylparaben, sodium benzoate, and potassium sorbate; and
   optionally, wherein based on 10 parts by weight of the lamotrigine particles, the preservative is 1-3 parts by weight.

9. The suspension according to anyone of technical solutions 1-8, further comprising a filler,
   optionally, wherein the filler is one or a combination of more of mannitol, microcrystalline cellulose, sucrose, and lactose; and
   optionally, wherein based on 10 parts by weight of the lamotrigine particles, the filler is 20-60 parts by weight.

10. The suspension according to anyone of technical solutions 1-9, further comprising a sweetener,
   optionally, wherein the sweetener is one or a combination of more of sucralose, aspartame, and sodium saccharin; and
   optionally, wherein based on 10 parts by weight of the lamotrigine particles, the sweetener is 1-3 parts by weight.

11. The suspension according to anyone of technical solutions 1-10, further comprising a preservative, a sweetener and a filler;
   optionally, wherein the preservative is one or a combination of more of sodium propylparaben, sodium methylparaben, sodium benzoate, and potassium sorbate; and/or wherein based on 10 parts by weight of the lamotrigine particles, the preservative is about 1-3 parts by weight;
   optionally, wherein the filler is one or a combination of more of mannitol, microcrystalline cellulose, sucrose, and lactose; and/or wherein based on 10 parts by weight of the lamotrigine particles, the filler is about 20-60 parts by weight;

optionally, wherein the sweetener is one or a combination of more of sucralose, aspartame, and sodium saccharin; and/or wherein based on 10 parts by weight of the lamotrigine particles, the sweetener is about 1-3 parts by weight.

12. The suspension according to anyone of technical solutions 1-11, wherein the suspension maintains at least uniformity and stability for 24 hours at a low temperature or normal temperature.

13. The suspension according to anyone of technical solutions 1-12, wherein the lamotrigine particles have a particle size (D90) of 4.5 μm or 8 μm, the lamotrigine hydrate form A in the suspension has a particle size of 20-30 μm, the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

14. The suspension according to anyone of technical solutions 1-13, wherein the suspension is applicable as a suspension.

15. The suspension according to anyone of technical solutions 1-14, wherein an appropriate pH modifier (in terms of type and/or content) is selected to provide a pH range such that the lamotrigine hydrate form A has the following increases in particle size: the particle size increased by less than 30%, less than 20%, less than 10% or less than 5% in the range of about Day 1, about Day 2, about Day 3, about Day 5, about Week 1, about Week 2, about Week 3, about Week 4, about Week 6 or about Week 8.

16. The suspension according to anyone of technical solutions 1-14, wherein the lamotrigine hydrate form A in the suspension has a particle size increasing in a range selected from the group consisting of the following: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

Technical Solution Group E:

1. A suspension, comprising
   (a) a lamotrigine hydrate form A having a particle size selected from the group consisting of one or more of the following ranges: 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm;
   (b) a pH modifier, which is such that the suspension has a pH selected from the group consisting of one or more of the following: 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH.

2. The suspension according technical solution 1, wherein the particle size (D90) is in a range of 8-10, 7-9, 7-8 or 8-9 μm, and meanwhile, an appropriate pH modifier (in terms of type and/or content) is selected such that the suspension has a pH in a range of: 4.6-6.8, 4.8-6.2, 4.8-6.0, 4.8-5.8 or 4.6-5.6.

3. The suspension according technical solution 1, wherein the particle size (D90) is in a range of 10-12, 11-13, 11-12 or 12-13 μm, and meanwhile, an appropriate pH modifier (in terms of type and/or content) is selected such that the suspension has a pH in a range of: 5.6-6.8, 5.8-6.8, 5.8-6.6, 6.0-6.8 or 6.0-6.6.

4. The suspension according to anyone of technical solutions 1-3, wherein an XRPD pattern of the lamotrigine hydrate form A comprises characteristic peaks at diffraction angles (2θ) of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles 2θ of about 15.9±0.2, 20.5±0.2, 23.5±0.2, 28.2±0.2, and 30.7±0.2 degrees; and/or,
   said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or
   wherein said XRPD pattern of said lamotrigine hydrate form A comprises characteristic peaks at diffraction angles 2θ substantially the same as diffraction angles shown in FIG. 1; or
   wherein said XRPD pattern of said lamotrigine hydrate form A has XRPD peak positions substantially the same as XRPD peak positions shown in FIG. 1; or
   wherein said XRPD pattern of said lamotrigine hydrate form A has XRPD peak positions the same as XRPD peak positions shown in FIG. 1.

5. The suspension according to anyone of technical solutions 1-4, wherein the lamotrigine particles have a particle size (D90) of about 4.5-8 μm, and the pH modifier has an amount such that the dry suspension is mixed with an aqueous phase to obtain a suspension having a pH of 4.6-6.9; and/or,
   based on 10 parts by weight of the lamotrigine particles, the pH modifier is 0.5-5.1 parts by weight; and/or,
   said pH modifier is selected from the group consisting of one or a combination of more of sodium dihydrogen phosphate, disodium hydrogen phosphate, citric acid, and sodium citrate.

6. The suspension according to anyone of technical solutions 1-4, wherein the lamotrigine particles have a particle size (D90) of about 12-13 μm, and the pH modifier has an amount such that the dry suspension is mixed with an aqueous phase to obtain a suspension having a pH of 5.8-6.9; and/or,
   based on 10 parts by weight of the lamotrigine particles, the pH modifier is 3-8 parts by weight; and/or,
   said pH modifier is selected from the group consisting of one or a combination of more of sodium dihydrogen phosphate, disodium hydrogen phosphate, citric acid, and sodium citrate.

7. The suspension according to anyone of technical solutions 1-6, wherein the suspension further comprises a thickener, and the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

optionally, said thickener is selected from the group consisting of xanthan gum, povidone, colloidal microcrystalline cellulose, sodium alginate and their combinations;

optionally, said thickener is xanthan gum; and/or based on 10 parts by weight of the lamotrigine particles, the thickener is 1-7 parts by weight.

8. The suspension according to anyone of technical solutions 1-7, wherein the suspension further comprises a combination of lamotrigine particles, a thickener, a pH modifier and a preservative;

optionally, wherein said preservative is one or a combination of more of sodium propylparaben, sodium methylparaben, sodium benzoate, and potassium sorbate; and optionally, wherein based on 10 parts by weight of the lamotrigine particles, the preservative is 1-3 parts by weight.

9. The suspension according to anyone of technical solutions 1-8, wherein the suspension further comprises a combination of lamotrigine particles, a thickener, a pH modifier and a filler;

optionally, wherein the filler is one or a combination of more of mannitol, microcrystalline cellulose, sucrose, and lactose; and optionally, wherein based on 10 parts by weight of the lamotrigine particles, the filler is 20-60 parts by weight.

10. The suspension according to anyone of technical solutions 1-9, wherein the suspension further comprises a combination of lamotrigine particles, a thickener, a pH modifier and a sweetener;

optionally, wherein the sweetener is one or a combination of more of sucralose, aspartame, and sodium saccharin; and optionally, wherein based on 10 parts by weight of the lamotrigine particles, the sweetener is 1-3 parts by weight.

11. The suspension according to anyone of technical solutions 1-10, wherein the suspension further comprises a combination of lamotrigine particles, a thickener, a pH modifier, a preservative, a sweetener and a filler;

optionally, wherein the preservative is one or a combination of more of sodium propylparaben, sodium methylparaben, sodium benzoate, and potassium sorbate; and/or wherein based on 10 parts by weight of the lamotrigine particles, the preservative is about 1-3 parts by weight;

optionally, wherein the filler is one or a combination of more of mannitol, microcrystalline cellulose, sucrose, and lactose; and/or wherein based on 10 parts by weight of the lamotrigine particles, the filler is about 20-60 parts by weight;

optionally, wherein the sweetener is one or a combination of more of sucralose, aspartame, and sodium saccharin; and/or wherein based on 10 parts by weight of the lamotrigine particles, the sweetener is about 1-3 parts by weight.

12. The suspension according to anyone of technical solutions 1-11, wherein the lamotrigine particles have a particle size (D90) of 4.5 μm or 8 μm, and the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

Technical Solution Group F:

1. A method for preparing a lamotrigine dry suspension, comprising the step of: mixing lamotrigine particles, a thickener and a pH modifier, wherein the lamotrigine particles have a particle size (D90) of 1-30 μm, and the pH modifier has an amount such that the dry suspension and an aqueous phase are mixed to subsequently obtain a suspension having a pH of 4.6-6.9.

2. The method according to technical solution 1, wherein the pH modifier is selected from the group consisting of one or a combination of more of sodium dihydrogen phosphate, disodium hydrogen phosphate, citric acid, and sodium citrate; and/or wherein based on 10 parts by weight of the lamotrigine particles, the pH modifier is 0.5-8 parts by weight.

3. The method according to anyone of technical solutions 1-2, wherein after the dry suspension is mixed with the aqueous phase to form the suspension, more than 80%, 85%, 90% or 95% of lamotrigine exists in a form of a lamotrigine hydrate form A; and/or after the dry suspension is mixed with the aqueous phase to form the suspension, the lamotrigine hydrate form A in the suspension has a particle size of 20-80 μm.

4. The method according to technical solution 3, wherein an XRPD pattern of the lamotrigine hydrate form A comprises characteristic peaks at diffraction angles 2θ of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles 2θ of about 15.9±0.2, 20.5=0.2, 23.5±0.2, 28.2±0.2, and 30.7±0.2 degrees; and/or, said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or wherein said XRPD pattern of said lamotrigine hydrate form A comprises characteristic peaks at diffraction angles 2θ substantially the same as diffraction angles shown in FIG. 1; or wherein said XRPD pattern of said lamotrigine hydrate form A has XRPD peak positions substantially the same as XRPD peak positions shown in FIG. 1; or wherein said XRPD pattern of said lamotrigine hydrate form A has XRPD peak positions the same as XRPD peak positions shown in FIG. 1.

5. The method according to anyone of technical solutions 1-4, wherein the lamotrigine particles have a particle size (D90) of about 4.5-8 μm, and the pH modifier has an amount such that the dry suspension is mixed with an aqueous phase to obtain a suspension having a pH of 4.6-6.9; and/or, based on 10 parts by weight of the lamotrigine particles, the pH modifier is 0.5-5.1 parts by weight; and/or, said pH modifier is selected from the group consisting of one or a combination of more of sodium dihydrogen phosphate, disodium hydrogen phosphate, citric acid, and sodium citrate.

6. The method according to anyone of technical solutions 1-4, wherein the lamotrigine particles have a particle size (D90) of about 12-13 μm, and the pH modifier has an amount such that the dry suspension is mixed with an aqueous phase to obtain a suspension having a pH of 5.8-6.9; and/or, based on 10 parts by weight of the lamotrigine particles, the pH modifier is 3-8 parts by weight; and/or, said pH modifier is selected from the group consisting of one or a combination of more of sodium dihydrogen phosphate, disodium hydrogen phosphate, citric acid, and sodium citrate.

7. The method according to anyone of technical solutions 1-6, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

optionally, said thickener is selected from the group consisting of xanthan gum, povidone, colloidal microcrystalline cellulose, sodium alginate and their combinations;

optionally, said thickener is xanthan gum; and/or based on 10 parts by weight of the lamotrigine particles, the thickener is 1-7 parts by weight.

8. The method according to anyone of technical solutions 1-7, further comprising mixing the lamotrigine particles, the thickener and the pH modifier with the preservative;

optionally, wherein said preservative is one or a combination of more of sodium propylparaben, sodium methylparaben, sodium benzoate, and potassium sorbate; and optionally, wherein based on 10 parts by weight of the lamotrigine particles, the preservative is 1-3 parts by weight.

9. The method according to anyone of technical solutions 1-8, further comprising mixing the lamotrigine particles, the thickener and the pH modifier with the filler.

optionally, wherein the filler is one or a combination of more of mannitol, microcrystalline cellulose, sucrose, and lactose; and optionally, wherein based on 10 parts by weight of the lamotrigine particles, the filler is 20-60 parts by weight.

10. The method according to anyone of technical solutions 1-9, further comprising mixing the lamotrigine particles, the thickener and the pH modifier with the sweetener, optionally, wherein the sweetener is one or a combination of more of sucralose, aspartame, and sodium saccharin; and optionally, wherein based on 10 parts by weight of the lamotrigine particles, the sweetener is 1-3 parts by weight.

11. The method according to anyone of technical solutions 1-10, further comprising mixing the lamotrigine particles, the thickener and the pH modifier with the preservative, the sweetener and the filler, optionally, wherein the preservative is one or a combination of more of sodium propylparaben, sodium methylparaben, sodium benzoate, and potassium sorbate;

and/or wherein based on 10 parts by weight of the lamotrigine particles, the preservative is about 1-3 parts by weight;

optionally, wherein the filler is one or a combination of more of mannitol, microcrystalline cellulose, sucrose, and lactose; and/or wherein based on 10 parts by weight of the lamotrigine particles, the filler is about 20-60 parts by weight;

optionally, wherein the sweetener is one or a combination of more of sucralose, aspartame, and sodium saccharin; and/or wherein based on 10 parts by weight of the lamotrigine particles, the sweetener is about 1-3 parts by weight.

12. The method according to anyone of technical solutions 1-11, wherein the lamotrigine particles have a particle size (D90) of 4.5 μm or 8 μm, and the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

13. A dry suspension prepared with the method according to anyone of technical solutions 1-12.

Technical Solution Group G:

1. A method for preparing a suspension comprising a lamotrigine hydrate form A, comprising the steps of:

(a-i) mixing lamotrigine particles, a thickener and a pH modifier, and adding a resulting mixture to an aqueous phase, or (a-ii) mixing lamotrigine particles and a thickener with an aqueous phase comprising a pH modifier, (b) dispersing uniformly, and standing at a low temperature to obtain the suspension comprising the lamotrigine hydrate form A, wherein the lamotrigine particles have a particle size (D90) of about 1-30 μm, wherein the low temperature is lower than about 25° C., wherein the suspension has a pH of 4.6-6.9, or the pH modifier has an amount such taht the suspension has a pH of 4.6-6.9.

2. The method according to technical solution 1, wherein the pH modifier is selected from the group consisting of one or a combination of more of sodium dihydrogen phosphate, disodium hydrogen phosphate, citric acid, and sodium citrate; and/or wherein based on 10 parts by weight of the lamotrigine particles, the pH modifier is 0.5-8 parts by weight.

3. The method according to anyone of technical solutions 1-2, wherein an XRPD pattern of the lamotrigine hydrate form A comprises characteristic peaks at diffraction angles (2θ) of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles 2θ of about 15.9±0.2, 20.5±0.2, 23.5±0.2, 28.2±0.2, and 30.7±0.2 degrees; and/or, said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or wherein said XRPD pattern of said lamotrigine hydrate form A comprises characteristic peaks at diffraction angles 2θ substantially the same as diffraction angles shown in FIG. 1; or wherein said XRPD pattern of said lamotrigine hydrate form A has XRPD peak positions substantially the same as XRPD peak positions shown in FIG. 1; or wherein said XRPD pattern of said lamotrigine hydrate form A has XRPD peak positions the same as XRPD peak positions shown in FIG. 1.

4. The method according to anyone of technical solutions 1-3, wherein the lamotrigine particles have a particle size (D90) of about 4.5-8 μm, and the pH modifier has an amount such that the suspension has a pH of about 4.6-6.9; and/or, based on 10 parts by weight of the lamotrigine particles, the pH modifier is 0.5-5.1 parts by weight; and/or, said pH modifier is selected from the group consisting of one or a combination of more of sodium dihydrogen phosphate, disodium hydrogen phosphate, citric acid, and sodium citrate.

5. The method according to anyone of technical solutions 1-3, wherein the lamotrigine particles have a particle size (D90) of about 12-13 μm, and the pH modifier has an amount such that the suspension has a pH of about 5.8-6.9; and/or, based on 10 parts by weight of the lamotrigine particles, the pH modifier is 3-8 parts by weight; and/or, said pH modifier is selected from the group consisting of one or a combination of more of sodium dihydrogen phosphate, disodium hydrogen phosphate, citric acid, and sodium citrate.

6. The method according to anyone of technical solutions 1-5, wherein more than about 80%, 85%, 90% or 95% of lamotrigine in the suspension exists in a form of the lamotrigine hydrate form A; and/or the lamotrigine hydrate form A in the suspension has a particle size of 20-80 μm.

7. The method according to anyone of technical solutions 1-6, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

optionally, said thickener is selected from the group consisting of xanthan gum, povidone, colloidal microcrystalline cellulose, sodium alginate and their combinations;

optionally, said thickener is xanthan gum; and/or based on 10 parts by weight of the lamotrigine particles, the thickener is 1-7 parts by weight.

8. The method according to anyone of technical solutions 1-7, further comprising mixing the lamotrigine particles, the thickener and the pH modifier with the preservative, and adding a resulting mixture to an aqueous phase, or mixing the lamotrigine particles and the thickener with an aqueous phase comprising the pH modifier and the preservative;

optionally, wherein said preservative is one or a combination of more of sodium propylparaben, sodium methylparaben, sodium benzoate, and potassium sorbate; and optionally, wherein based on 10 parts by weight of the lamotrigine particles, the preservative is 1-3 parts by weight.

9. The method according to anyone of technical solutions 1-8, further comprising mixing the lamotrigine particles, the thickener and the pH modifier with the filler, and adding a resulting mixture to an aqueous phase, or mixing the lamotrigine particles and the thickener with an aqueous phase comprising the pH modifier and the filler;

optionally, wherein the filler is one or a combination of more of mannitol, microcrystalline cellulose, sucrose, and lactose; and optionally, wherein based on 10 parts by weight of the lamotrigine particles, the filler is 20-60 parts by weight.

10. The method according to anyone of technical solutions 1-9, further comprising mixing the lamotrigine particles, the thickener and the pH modifier with the sweetener, and adding a resulting mixture to an aqueous phase, or mixing the lamotrigine particles and the thickener with an aqueous phase comprising the pH modifier and the sweetener;

optionally, wherein the sweetener is one or a combination of more of sucralose, aspartame, and sodium saccharin; and optionally, wherein based on 10 parts by weight of the lamotrigine particles, the sweetener is 1-3 parts by weight.

11. The method according to anyone of technical solutions 1-10, further comprising mixing the lamotrigine particles, the thickener and the pH modifier with the preservative, the sweetener and the filler, and adding a resulting mixture to an aqueous phase, or mixing the lamotrigine particles and the thickener with an aqueous phase comprising the pH modifier, the preservative, the sweetener and the filler;

optionally, wherein the preservative is one or a combination of more of sodium propylparaben, sodium methylparaben, sodium benzoate, and potassium sorbate; and/or wherein based on 10 parts by weight of the lamotrigine particles, the preservative is about 1-3 parts by weight;

optionally, wherein the filler is one or a combination of more of mannitol, microcrystalline cellulose, sucrose, and lactose; and/or wherein based on 10 parts by weight of the lamotrigine particles, the filler is about 20-60 parts by weight;

optionally, wherein the sweetener is one or a combination of more of sucralose, aspartame, and sodium saccharin; and/or wherein based on 10 parts by weight of the lamotrigine particles, the sweetener is about 1-3 parts by weight.

12. The method according to anyone of technical solutions 1-11, wherein the dispersing uniformly is implemented by mechanical stirring, magnetic stirring, and/or manual shaking for about 1-120 minutes.

13. The method according to anyone of technical solutions 1-12, wherein the low temperature is lower than about 25° C.; and preferably, the standing at a low temperature is performed for at least about 30 minutes.

14. The method according to anyone of technical solutions 1-13, wherein the dispersing uniformly is separated by a time interval of up to about 12 hours from the standing at a low temperature.

15. The method according to anyone of technical solutions 1-14, wherein the lamotrigine particles have a particle size (D90) of 4.5 μm or 8 μm, the lamotrigine hydrate form A in the suspension has a particle size of 20-30 μm, the thickener is xanthan gum, and based on 10 parts by weight of the lamotrigine particles, the xanthan gum is 3 parts by weight; the pH modifier is a combination of disodium hydrogen phosphate and citric acid, and based on 10 parts by weight of the lamotrigine particles, the pH modifier is 4 parts by weight, optionally the disodium hydrogen phosphate is 1.5 parts by weight and the citric acid is 2.5 parts by weight; the preservative is a combination of sodium propylparaben and sodium methylparaben, wherein based on 10 parts by weight of the lamotrigine particles, the preservative is 2.2 parts by weight, optionally, the sodium propylparaben is 0.2 parts by weight and the sodium methylparaben is 2.0 parts by weight; the filler is mannitol, and based on 10 parts by weight of the lamotrigine particles, the filler is 20 parts by weight; and the sweetener is sucralose, and based on 10 parts by weight of the lamotrigine particles, the sweetener is 1 part by weight.

16. A suspension prepared with the method according to anyone of technical solutions 1-15.

17. The method according to anyone of technical solutions 1-16, wherein the suspension is applicable as a suspension.

18. The method according to anyone of technical solutions 1-17, further comprising filtering the suspension to obtain the lamotrigine hydrate form A; and optionally, further comprising washing crystals with water during filtering to remove a thickener adhered to the crystals.

19. The suspension according to anyone of technical solutions 1-18, wherein an appropriate pH modifier (in terms of type and/or content) is selected to provide a pH range such that the lamotrigine hydrate form A has the following increases in particle size: the particle size increased by less than 30%, less than 20%, less than 10% or less than 5% in the range of about Day 1, about Day 2, about Day 3, about Day 5, about Week 1, about Week 2, about Week 3, about Week 4, about Week 6 or about Week 8.

20. The suspension according to anyone of technical solutions 1-19, wherein a particle size (D90) of the lamotrigine particles is selected to provide a range such that the lamotrigine hydrate form A in the suspension has the following increases in particle size: the particle size increased by less than 150%, less than 100%, less than 80%, less than 50%, less than 30%, less than 20%, less than 10% or less than 5% in the range of about Day 1, about Day 2, about Day 3, about Day 5, about Week 1, about Week 2, about Week 3, about Week 4, about Week 6 or about Week 8.

Technical Solution Group H:

1. A method for preparing a suspension comprising a lamotrigine hydrate form A, wherein the lamotrigine hydrate form A has a particle size selected from the group consisting of the following: 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm, wherein the method comprises the steps of:

(a) adding lamotrigine particles and a thickener to an aqueous phase, wherein the lamotrigine particles have a particle size (D90) selected from the group consisting of one or more of the following: about 4.5 μm, 4.6 μm, 4.7 μm, 4.8 μm, 4.9 μm, 5.3 μm, 5.1 μm, 5.2 μm, 5.3 μm, 5.4 μm, 5.5 μm, 5.6 μm, 5.7 μm, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, 7.0 μm, 7.1 μm, 7.2 μm, 7.3 μm, 7.4 μm, 7.5 μm, 7.6 μm, 7.7 μm, 7.8 μm, 7.9 μm and 8.0 μm, and a particle size (D90) range consisting of any two of the preceding particles sizes (D90s); and (b) dispersing the lamotrigine particles having the particle size (D90) and the thickener in an aqueous phase uniformly; cooling the aqueous phase to a temperature of lower than about 25° C. to obtain a suspension comprising the lamotrigine hydrate form A.

2. The method according to technical solution 1, further comprising adding a pH modifier, wherein an appropriate pH modifier (in terms of type and/or content) is selected such that the suspension obtained by reconstituting the lamotrigine particles in an aqueous phase has a pH selected from the group consisting of one or more of the following: 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH;

optionally, an appropriate pH modifier (in terms of type and/or content) is selected to control such that a suspension obtained by reconstituting the lamotrigine particles in an aqueous phase has a particle size selected from the group consisting of one or more of the following ranges: 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm;

optionally, an appropriate pH modifier (in terms of type and/or content) is selected to control such that a suspension obtained by reconstituting the lamotrigine particles in an aqueous phase has stability defined by the previous solutions.

3. The method according to technical solution 1 or 2, further comprising adding a preservative.

4. The method according to anyone of technical solutions 1-2, further comprising cooling the aqueous phase to a temperature lower than about 20° C., lower than about 10° C., lower than 4° C., or lower than 0° ° C. to obtain a suspension comprising the lamotrigine hydrate form A.

5. The method according to anyone of technical solutions 1-4, wherein more than 80%, 85%, 90% or 95% of lamotrigine in the suspension exists in a form of the lamotrigine hydrate form A.

Technical Solution Group I:

1. A method for preparing a suspension of a lamotrigine hydrate form A, wherein the lamotrigine hydrate form A mataines the particles size within the range of 20-80 μm within at least one week, and has the antimicrobial stability of at least one month according to USP<51>. The method comprises the steps of:

(a) adding lamotrigine particles having a particle size (D90) of 1-30 μm, a pH modifier and a preservative to an aqueous phase; and (b) dispersing the lamotrigine particles, the pH modifier and the preservative in the aqueous phase uniformly; cooling the aqueous phase to a temperature of lower than about 25° C. to obtain a suspension comprising the lamotrigine hydrate form A.

Technical Solution Group J:

1. A method for preparing a suspension of a lamotrigine hydrate form A, comprising the steps of: adding lamotrigine particles and a thickener to an aqueous phase; dispersing uniformly; and standing at a low temperature to obtain a suspension comprising the lamotrigine hydrate form A, wherein the lamotrigine particles have a particle size (D90) of about 1-30 μm, wherein the low temperature is lower than about 25° C.; and wherein an XRPD pattern of the lamotrigine hydrate form A comprises characteristic peaks at diffraction angles (2θ) of about 11.5±0.2, 13.4±0.2, 15.0±0.2, 16.5±0.2, 19.2±0.2, 26.9±0.2, and 27.7±0.2 degrees, and has no characteristic peak(s) at one or more of diffraction angles (2θ) of about 15.9±0.2, 20.5±0.2, 23.5±0.2, 28.2±0.2, and 30.7±0.2 degrees, or, the XRPD pattern of the lamotrigine hydrate form A has no characteristic peak at diffraction angles (2θ) of about 15.9±0.2, 20.5±0.2, 23.5±0.2, 28.2±0.2 and 30.7±0.2 degrees; or the XRPD pattern of the lamotrigine hydrate form A comprises characteristic peaks at diffraction angles (2θ) substantially the same as diffraction angles shown in FIG. 1; or the XRPD pattern of the lamotrigine hydrate form A is substantially the same as that shown in FIG. 1; and optionally, the lamotrigine hydrate form A has a purity of at least about 80%, at least about 90%, at least about 95% or is substantially pure.

2. The method according to technical solution 1, comprising the step of selecting the particle size (D90) of the lamotrigine particles, such that the lamotrigine hydrate form A in the suspension has a particle size selected from the group consisting of the following one or more ranges: 20-80 μm, 20-70 μm, 20-60 μm, 20-50 μm, 20-40 μm, 20-30 μm, 30-80 μm, 30-70 μm, 30-60 μm, 30-50 μm, 30-40 μm, 40-80 μm, 40-70 μm, 40-60 μm, 40-50 μm, 50-80 μm, 50-70 μm, 50-60 μm, 60-80 μm, 60-70 μm and 70-80 μm.

3. A method for preparing a lamotrigine hydrate form A, comprising filtering the suspension of technical solution 1 to obtain the lamotrigine hydrate form A.

4. The method according to anyone of technical solutions 1-3, wherein the lamotrigine particles have a particle size (D90) of about 4.5-30 μm, about 4.5-20 μm, about 8-12 μm, about 4.5-8 μm, or 12-13 μm;

optionally, wherein the suspension has a pH value of 4.6-6.9, 5.8-6.9 or 5.5-6.5; or the suspension has a pH selected from the group consisting of one or more of the following: about 4.6, 4.7, 4.8, 4.9, 5.3, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.85 and 6.9, and a pH range consisting of any two of the preceding pH.

5. The method according to anyone of technical solutions 1-4, wherein the thickener is selected from the group consisting of: hydrolyzed colloids, such as xanthan gum, guar gum, locust bean gum, and carrageenan; cellulose derivatives, such as sodium carboxymethylcellulose, hydroxypropyl cellulose, methylcellulose, and hydroxypropyl methylcellulose; polysaccharides, such as starch and pregelatinized starch; alginates, such as sodium alginate; acrylic copolymers, such as carbomer; and magnesium aluminum silicate, and their combinations;

preferably, the thickener is selected from the group consisting of xanthan gum, povidone, colloidal microcrystalline cellulose, sodium alginate and their combinations;

preferably, the thickener is xanthan gum; and preferably, based on about 10 parts by weight of the lamotrigine particles, the thickener is about 1-7 parts by weight, and preferably, about 1-5 parts by weight.

6. The method according to anyone of technical solutions 1-6, wherein the aqueous phase is purified water or comprises purified water and one or more of the following: an essence, a pH modifier and a sweetener; and preferably, based on about 10 parts by weight of the lamotrigine particles, the aqueous phase is about 100-5000 parts by weight, more preferably, about 500-2000 parts by weight.

7. The method according to anyone of technical solutions 1-6, wherein the dispersing uniformly is implemented by mechanical stirring, magnetic stirring, and/or manual shaking for about 1-120 minutes, preferably 3-15 minutes.

8. The method according to anyone of technical solutions 1-7, wherein the low temperature is lower than about 25° C., preferably lower than about 20° C.;

preferably, the standing at a low temperature is implemented for at least about 30 minutes, more preferably at least about 2 hours.

9. The method according to anyone of technical solutions 1-8, wherein the dispersing uniformly is separated by a time interval of up to about 12 hours, preferably up to about 1 minute, and more preferably 0, from the standing at a low temperature.

10. The method according to anyone of technical solutions 1-9, wherein the suspension is applicable as a suspension; and preferably, the method further comprises preparing lamotrigine particles and a thickener together with one or more of a filler, a sweetener, a pH modifier and a preservative into a dry suspension, which is then added to the aqueous phase; and preferably, the dry suspension is prepared by direct mixing.

11. The method according to technical solution 10, wherein the filler is one or a combination of more of mannitol, microcrystalline cellulose, sucrose, and lactose; and preferably, based on 10 parts by weight of the lamotrigine particles, the filler is about 20-60 parts by weight;

the sweetener is one or a combination of more of sucralose, aspartame, and sodium saccharin; and preferably, based on 10 parts by weight of the lamotrigine particles, the sweetener is about 1-3 parts by weight;

the pH modifier is one or a combination of more of sodium dihydrogen phosphate, disodium hydrogen phosphate, citric acid, and sodium citrate, and preferably, based on about 10 parts by weight of the lamotrigine particles, the pH modifier is about 0.5-8 parts by weight, about 0.5-5.1 parts by weight, about 3-8 parts by weight, or about 2-5 parts by weight; and the preservative is one or a combination of more of sodium propylparaben, sodium methylparaben, sodium benzoate, and potassium sorbate, and preferably, based on about 10 parts by weight of the lamotrigine particles, the preservative is about 1-3 parts by weight.

12. The method according to anyone of technical solutions 1-11, wherein more than about 80% of lamotrigine exists in a form of the lamotrigine hydrate form A; preferably, more than about 90% of lamotrigine exists in a form of the lamotrigine hydrate form A; more preferably, more than about 95% of lamotrigine exists in a form of the lamotrigine hydrate form A; and most preferably, more than about 97% of lamotrigine exists in a form of the lamotrigine hydrate form A.

13. A composition, comprising the suspension comprising the lamotrigine hydrate form A according to anyone of technical solutions 1-12 and one or more pharmaceutically acceptable excipients.

14. The composition according to technical solution 13, further comprising one or more additional medicaments selected from the group consisting of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

15. The composition according to technical solution 13 or 14, wherein the composition is in a dosage form selected from the group consisting of a tablet, a capsule, a powder and a suspension, and preferably a suspension.

16. The composition according to anyone of technical solutions 13-15, wherein in the composition, more than about 80% of lamotrigine exists in a form of the lamotrigine hydrate form A; preferably, more than about 90% of lamotrigine exists in a form of the lamotrigine hydrate form A; and more preferably, more than about 95% of lamotrigine exists in a form of the lamotrigine hydrate form A.

17. The composition according to anyone of technical solutions 13-16, wherein the pharmaceutically acceptable excipients are selected from the group consisting of one or more of a thickener, a filler, a sweetener, a pH modifier and a preservative;

preferably, the thickener is selected from the group consisting of one or more of xanthan gum, povidone, colloidal microcrystalline cellulose and sodium alginate, more preferably xanthan gum; and preferably, the content of the thickener is about 1 to 7 parts by weight, preferably about 1 to 5 parts by weight, on the basis that the content of the lamotrigine hydrate form A is about 10 parts by weight;

preferably, the filler is selected from the group consisting of one or more of mannitol, microcrystalline cellulose, sucrose and lactose; and preferably, the content of the filler is about 20 to 60 parts by weight, on the basis that the content of the lamotrigine hydrate form A is about 10 parts by weight;

preferably, the sweetener is selected from the group consisting of one or more of sucralose, aspartame and sodium saccharin; and preferably, the content of the sweetener is about 1-3 parts by weight, on the basis that content of the lamotrigine hydrate form A is about 10 parts by weight;

preferably, the pH modifier is selected from the group consisting of one or more of sodium dihydrogen phosphate, disodium hydrogen phosphate, citric acid and sodium citrate; and preferably, the content of the pH modifier is about 0.5-8 parts by weight, about 0.5-5.1 parts by weight, about 3-8 parts by weight, or about 2-5 parts by weight, on the basis that the content of the lamotrigine hydrate form A is about 10 parts by weight; and preferably, the preservative is selected from the group consisting of one or more of sodium propylparaben, sodium methylparaben, sodium benzoate and potassium sorbate; and preferably, the content of the preservative is about 1 to 3 parts by weight, on the basis that the content of the lamotrigine hydrate form A is about 10 parts by weight.

18. The composition according to anyone of technical solutions 13-17, comprising:

about 10 parts by weight of the lamotrigine hydrate form A;

about 1-5 parts by weight of xanthan gum;

about 20-60 parts by weight of mannitol;

about 1-3 parts by weight of sucralose;

about 2-5 parts by weight of sodium dihydrogen phosphate, about 2-5 parts by weight of disodium hydrogen phosphate, and/or about 2-5 parts by weight of critic acid; and about 1-3 parts by weight of a combination of sodium methylparaben and sodium propylparaben, wherein a weight ratio of the sodium methylparaben to the sodium propylparaben is about 9:1.

19. Use of the compound according to anyone of technical solutions 13-18 in preparation of a medcament for treating a nervous system disease.

20. The use according to technical solution 19, wherein the nervous system disease is selected from the group consisting of one or more of Alzheimer's disease, depression, multiple sclerosis, Parkinson's disease, and epilepsy.

21. The use according to technical solution 19 or 20, wherein the medicament is for use in treatment of the nervous system disease in combination with an additional mediament, and preferably, the additional medicament is selected from the group consisting of one or more of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

22. The use according to anyone of technical solutions 19-21, wherein the medicament is in a form of suspension.

23. The use according to anyone of technical solutions 19-22, wherein in the medicament, more than about 80% of lamotrigine exists in a form of the lamotrigine hydrate form A; preferably, more than about 90% of lamotrigine exists in a form of the lamotrigine hydrate form A; and more preferably, more than about 95% of lamotrigine exists in a form of the lamotrigine hydrate form A.

Technical Solution Group K:

1. A pharmaceutical cartridge, comprising the pharmaceutical composition according to anyone of technical solution groups A, B and C, the suspension according to anyone of technical solution groups D and E, the dry suspension according to technical solution group F, and the suspension according to anyone of technical solution groups G, H, I and J, wherein the lamotrigine and other ingredients (for example, selected from the group consisting of one or more of a pH modifier, a preservative, a thickener, a filler, a sweetener, etc.) in the previously described technical solutions are contained in the same container;

or the lamotrigine and other ingredients (for example, selected from the group consisting of one or more of a pH modifier, a preservative, a thickener, a filler, a sweetener, etc.) mentioned in the previously described technical solutions are contained in one or more different containers;

optionally, the lamotrigine particles in the pharmaceutical cartridge can be mixed with other ingredients (for example, selected from the group consisting of one or more of a pH modifier, a preservative, a thickener, a filler, a sweetener, etc.) and then added to water to formulate a suspension; or the lamotrigine particles in the pharmaceutical cartridge can be mixed with an aqueous solution containing other ingredients (for example, selected from the group consisting of one or more of a pH modifier, a preservative, a thickener, a filler, a sweetener, etc.) to formulate a suspension; and optionally, the suspension, the dry suspension, the lamotrigine and, for example, the pH regulator, the preservative, the thickener, the filler, the sweetener, etc. are defined as described in the preceding sections herein in terms of type, content, D90 particle size, microscopic particle size, anti-microbial stability or the like.

Technical Solution Group L:

1. Use of the pharmaceutical composition according to anyone of technical solution groups A, B and C, the suspension according to anyone of technical solution groups D and E, the dry suspension according to technical solution group F, and the suspension according to anyone of technical solution groups G, H, I and J in preparation of a medicament or pharmaceutical cartridge for treating a nervous system disease.

2. The use according to technical solution 1, wherein the nervous system disease is selected from the group consisting of one or more of Alzheimer's disease, depression, multiple sclerosis, Parkinson's disease, and epilepsy.

3. The use according to technical solution 1 or 2, wherein the medicament is for use in treatment of the nervous system disease in combination with an additional mediament, and optionally, the additional medicament is selected from the group consisting of one or more of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

Technical Solution Group M:

1. A method for treating a nervous system disease, comprising administering a therapeutically effective amount of the pharmaceutical composition according to anyone of technical solution groups A, B and C, the suspension according to anyone of technical solution groups D and E, the dry suspension according to technical solution group F, and the suspension according to anyone of technical solution groups G, H, I and J to an individual in need thereof.

2. The method according to technical solution 1, wherein the nervous system disease is selected from the group consisting of one or more of Alzheimer's disease, depression, multiple sclerosis, Parkinson's disease, and epilepsy.

3. The method according to technical solution 1 or 2, further comprising administering a therapeutically effective amount of an additional mediament for treating the nervous system disease to an individual in need thereof, wherein optionally, the additional medicament is selected from the group consisting of one or more of oxcarbazpin, carbamazpin, phnytoin, valproic acid, thosuximid, flbamat, gabapntin, lvtiractam, tiagabin, prgabalin, phnobarbital, zonisamid, clonazpam, phnytoin, valproat, clobazam, vigabatrin, topiramat, and lacaramid.

4. The method according to anyone of technical solutions 1-3, wherein the dosage form is selected from the group consisting of one or more of: (a) a dosage form for oral administration, including a capsule, a tablet, a granule, a spray, a syrup and the like; (b) a dosage form for non-oral administration, such as rectal, vaginal, urethral, intraocular, nasal or ear administration, including an aqueous suspension, an oily preparation and the like, or drops, a spray, suppositories, paste, ointments, etc.; (c) a dosage form for administration through for example subcutaneous, intraperitoneal, intravenous, intramuscular, intradermal, intraorbital, intracapsular, intramedullary and intrasternal injection; and (d) a dosage form for local administration, including an inhalation solution, a nasal spray, an implant, and the like; and optionally, the dosage form is oral administration.

5. The method according to anyone of technical solutions 1-4, wherein the pharmaceutical composition according to anyone of technical solution groups A, B and C, the suspension according to anyone of technical solution groups D and E, the dry suspension according to technical solution group F, or the suspension according to anyone of technical solution groups G, H, I and J is administered one to four times per day in a single dose or multiple doses.

6. The method according to anyone of technical solutions 1-5, wherein the pharmaceutical composition according to anyone of technical solution groups A, B and C, the suspension according to anyone of technical solution groups D and E, the dry suspension according to technical solution group F, or the suspension according to anyone of technical solution groups G, H, I and J is administered in a dose range from 0.1 mg of the lamotrigine hydrate form A per kilogram of patient weight to 1000 mg of the lamotrigine hydrate form A per kilogram of patient weight.

7. The method according to anyone of technical solutions 1-6, wherein the dosage form is oral administration at a dose from 1 mg to 500 mg, or from 5 mg to 200 mg; or the dosage form is intravenous, subcutaneous or intramuscular injection at a dose from 0.01 mg to 100 mg, or from 0.1 mg to 60 mg.

8. The method according to anyone of technical solutions 1-8, wherein after administration, the pharmaceutical composition according to anyone of technical solution groups A, B and C, the suspension according to anyone of technical solution groups D and E, the dry suspension according to technical solution group F, or the suspension according to anyone of technical solution groups G, H, I and J has a release time from 1 hour to 12 hours, from 3 hours to 12 hours, or from 6 hours to 12 hours.

9. The method according to anyone of technical solutions 1-8, wherein the pharmaceutical composition according to anyone of technical solution groups A, B and C, the suspension according to anyone of technical solution groups D and E, the dry suspension according to technical solution group F, or the suspension according to anyone of technical solution groups G, H, I and J and the additional medicament are packaged in one pharmaceutical cartridge, or packaged indivdually and separately.

10. The method according to anyone of technical solutions 1-9, wherein the pharmaceutical composition according to anyone of technical solution groups A, B and C, the suspension according to anyone of technical solution groups D and E, the dry suspension according to technical solution group F, or the suspension according to anyone of technical solution groups G, H, I and J and the additional medicament are administrated to a patient simultaneously or successively.

The invention claimed is:

1. A pharmaceutical composition, comprising a therapeutically effective amount of anhydrous lamotrigine particles and one or more pharmaceutically acceptable excipients, wherein said anhydrous lamotrigine particles have a particle size D90 of about 4.5 to about 8 μm, and said excipients comprise a thickener and a pH modifier, wherein the pharmaceutical composition is in the form of a dry mixture, wherein said pH modifier provides a pH of about 4.6 to about 6.9 after said pharmaceutical composition is reconstituted with water to form a suspension, wherein the D90 of the anhydrous lamotrigine particles and the pH modifier are selected so that more than about 90% of lamotrigine from the anhydrous lamotrigine particles exists in lamotrigine hydrate form A in the suspension, wherein the hydrate form A has a particle size of 20-30 μm, wherein an XRPD pattern of said lamotrigine hydrate form A comprises characteristic peaks at diffraction angles 2θ of about 11.5±0.2, 13.4±0.2, 15.3±0.2, 16.5±0.2, 19.2±0.2, 26.9±0.2, and 27.7±0.2 degrees, and has no characteristic peak(s) at one or more of diffraction angles 2θ of about 15.9±0.2, 20.5±0.2, 23.5±0.2, 28.2±0.2, and 30.7±0.2 degrees; and/or, said XRPD pattern of said lamotrigine hydrate form A has no characteristic peaks at diffraction angles 2θ of about 15.9±0.2, 20.5±0.2, 23.5±0.2, 28.2±0.2 and 30.7±0.2 degrees; or wherein said XRPD pattern of said lamotrigine hydrate form A comprises characteristic peaks at diffraction angles 2θ substantially the same as diffraction angles shown in FIG. 1; or wherein said XRPD pattern of said lamotrigine hydrate form A has XRPD peak positions substantially the same as XRPD peak positions shown in FIG. 1; or wherein said XRPD pattern of said lamotrigine hydrate form A has XRPD peak positions the same as XRPD peak positions shown in FIG. 1.

2. The pharmaceutical composition according to claim 1, wherein said thickener is selected from the group consisting of: xanthan gum, guar gum, locust bean gum, and carrageenan; sodium carboxymethylcellulose, hydroxypropyl cellulose, methylcellulose, hydroxypropyl methylcellulose, pregelatinized starch, alginates, carbomer, magnesium aluminum silicate, and their combinations;

based on about 10 parts by weight of said anhydrous lamotrigine particles, said thickener is about 1-7 parts by weight.

3. The pharmaceutical composition according to claim 1, further comprising a preservative, wherein said preservative is selected from the group consisting of sodium propylparaben, sodium methylparaben, sodium benzoate, potassium sorbate, and a combination thereof; and optionally, wherein based on about 10 parts by weight of said anhydrous lamotrigine particles, said preservative is about 1-3 parts by weight.

4. The pharmaceutical composition according to claim 1, wherein an appropriate particle size D90 of the anhydrous lamotrigine particles is selected such that said lamotrigine hydrate form A formed after said dry mixture is formulated into said suspension has a pH range in said suspension leading to an increase in particle size by less than 100% in about 4 weeks.

5. The pharmaceutical composition according to claim 1, wherein an appropriate pH range corresponding to said pH modifier is selected such that said lamotrigine hydrate form A formed after said dry mixture is formulated into said suspension has a pH range in said suspension leading to an increase by less than 100%, in about 4 weeks.

6. The pharmaceutical composition according to claim 1, further comprising a preservative, a sweetener, and a filler, wherein said preservative is selected from the group consisting of sodium propylparaben, sodium methylparaben, sodium benzoate, potassium sorbate, and a combination thereof, and/or wherein based on about 10 parts by weight of said anhydrous lamotrigine particles, said preservative is about 1-3 parts by weight;

wherein said filler is selected from the group consisting of mannitol, microcrystalline cellulose, sucrose, lactose, and a combination thereof;

and/or wherein based on about 10 parts by weight of said anhydrous lamotrigine particles, said filler is about 20-60 parts by weight; and wherein said sweetener is selected from the group consisting of more of sucralose, aspartame, sodium saccharin, and a combination thereof, and/or based on about 10 parts by weight of said anhydrous lamotrigine particles, said sweetener is about 1-3 parts by weight.

7. The pharmaceutical composition according to claim 1, wherein said thickener is xanthan gum, and based on 10 parts by weight of said anhydrous lamotrigine particles, said xanthan gum is 3 parts by weight; said pH modifier is a combination of disodium hydrogen phosphate and citric acid, and based on 10 parts by weight of said anhydrous lamotrigine particles, said pH modifier is 4 parts by weight, optionally said disodium hydrogen phosphate is 1.5 parts by weight and said citric acid is 2.5 parts by weight; said preservative is a combination of sodium propylparaben and sodium methylparaben, wherein based on 10 parts by weight of said anhydrous lamotrigine particles, said preservative is 2.2 parts by weight, optionally, said sodium propylparaben is 0.2 parts by weight and said sodium methylparaben is 2.0 parts by weight; said filler is mannitol, and based on 10 parts by weight of said anhydrous lamotrigine particles, said filler is 20 parts by weight; and said sweetener is sucralose, and based on 10 parts by weight of said anhydrous lamotrigine particles, said sweetener is 1 part by weight.

8. A suspension prepared from the pharmaceutical composition of claim 1.

9. A method of treating a neurological disorder in a subject, comprising administering a suspension prepared from the pharmaceutical composition of claim 1 to the subject in need thereof.

10. The method of claim 9, wherein the neurological disorder is selected from one or more of Alzheimer's disease, depression, multiple sclerosis, Parkinson's disease, and epilepsy.

11. The method of claim 9, further comprising administering to the subject an agent selected from the group consisting of valproate, vigabatrin, oxcarbazepine, carbamazepine, topiramate, and lacosamide.

12. The pharmaceutical composition of claim 1, wherein said thickener is xanthan gum.

13. The pharmaceutical composition of claim 1, wherein said pH modifier provides a pH of about 4.6 to about 5.6 after said pharmaceutical composition is reconstituted with water to form a suspension.

* * * * *